(12) United States Patent
Jeong et al.

(10) Patent No.: US 11,041,073 B2
(45) Date of Patent: Jun. 22, 2021

(54) COMPOUND, CORE-SHELL DYE, PHOTOSENSITIVE RESIN COMPOSITION INCLUDING THE SAME, AND COLOR FILTER

(71) Applicant: SAMSUNG SDI CO., LTD., Yongin-si (KR)

(72) Inventors: Euisoo Jeong, Suwon-si (KR); Chaewon Pak, Suwon-si (KR); Hyewon Seo, Suwon-si (KR); Myoungyoup Shin, Suwon-si (KR); Sunwoong Shin, Suwon-si (KR); Kyubuem Choi, Suwon-si (KR); Gyuseok Han, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 366 days.

(21) Appl. No.: 16/308,853

(22) PCT Filed: May 12, 2017

(86) PCT No.: PCT/KR2017/004956
§ 371 (c)(1),
(2) Date: Dec. 11, 2018

(87) PCT Pub. No.: WO2018/056546
PCT Pub. Date: Mar. 29, 2018

(65) Prior Publication Data
US 2019/0256713 A1 Aug. 22, 2019

(30) Foreign Application Priority Data
Sep. 26, 2016 (KR) .................. 10-2016-0123227

(51) Int. Cl.
| | | |
|---|---|---|
| *C09B 57/00* | (2006.01) | |
| *G02B 5/20* | (2006.01) | |
| *G03F 7/027* | (2006.01) | |
| *C09B 55/00* | (2006.01) | |
| *C09B 67/00* | (2006.01) | |
| *G02B 5/22* | (2006.01) | |
| *G03F 7/00* | (2006.01) | |
| *G03F 7/031* | (2006.01) | |
| *G03F 7/033* | (2006.01) | |
| *C07D 471/14* | (2006.01) | |
| *C07C 233/78* | (2006.01) | |
| *C07C 211/64* | (2006.01) | |
| *C07D 257/10* | (2006.01) | |
| *G03F 7/105* | (2006.01) | |

(52) U.S. Cl.
CPC .......... *C09B 55/002* (2013.01); *C07C 211/64* (2013.01); *C07C 233/78* (2013.01); *C07D 257/10* (2013.01); *C07D 471/14* (2013.01); *C09B 57/00* (2013.01); *C09B 57/007* (2013.01); *C09B 67/0001* (2013.01); *G02B 5/22* (2013.01); *G02B 5/223* (2013.01); *G03F 7/0007* (2013.01); *G03F 7/031* (2013.01); *G03F 7/033* (2013.01); *G03F 7/105* (2013.01); *G03F 7/027* (2013.01)

(58) Field of Classification Search
CPC ........ G03F 7/0007; G03F 7/027; G03F 7/028; G03F 7/032; G03F 7/105; C07C 211/64; C09B 57/00; C09B 57/07; C09B 55/002
USPC .................................................. 430/7, 281.1
See application file for complete search history.

(56) References Cited

U.S. PATENT DOCUMENTS

| | | | |
|---|---|---|---|
| 8,273,875 B2 | 9/2012 | Smith et al. | |
| 2009/0068113 A1 | 3/2009 | Danaboyina et al. | |
| 2012/0296085 A1 | 11/2012 | Smith | |
| 2014/0198285 A1* | 7/2014 | Fujita | ..................... G03F 7/0275 349/106 |
| 2014/0349220 A1* | 11/2014 | Moon | ................... G03F 7/0007 430/7 |

FOREIGN PATENT DOCUMENTS

| | | |
|---|---|---|
| EP | 2 129 788 B1 | 9/2014 |
| JP | 59-125735 A | 7/1984 |
| JP | 06-041458 A | 2/1994 |
| JP | H06-21231 B2 | 3/1994 |
| JP | H06-44160 B2 | 6/1994 |
| JP | H07-27245 B2 | 3/1995 |
| JP | 07-140654 A | 6/1995 |
| JP | 2546302 B2 | 10/1996 |
| JP | 10-254133 A | 9/1998 |
| JP | 2003-109676 * | 4/2003 |
| JP | 2005-126587 A | 5/2005 |
| JP | 2009-015113 A | 1/2009 |
| JP | 2009-036811 A | 2/2009 |
| JP | 2012-158621 A | 8/2012 |
| JP | 2015-230416 A | 12/2015 |
| JP | 2016-117858 A | 6/2016 |
| KR | 10-1999-0007097 A | 1/1999 |
| KR | 10-2002-0015650 A | 2/2002 |
| KR | 10-2005-0020653 A | 3/2005 |
| KR | 10-2009-0106226 A | 10/2009 |
| KR | 10-2010-0078845 A | 7/2010 |

(Continued)

OTHER PUBLICATIONS

Computer-generated translation of JP 2003-109676 (Apr. 2003) (Year: 2003).*

(Continued)

*Primary Examiner* — John A McPherson
(74) *Attorney, Agent, or Firm* — Lee IP Law, P.C.

(57) ABSTRACT

A compound represented by specific chemical formula, a core including the same, a core-shell dye including a shell surrounding the core, a photosensitive resin composition including the same, and a color filter manufactured using the photosensitive resin composition are disclosed.

20 Claims, 1 Drawing Sheet

(56) References Cited

FOREIGN PATENT DOCUMENTS

| | | |
|---|---|---|
| KR | 10-2010-0080142 A | 7/2010 |
| KR | 10-2011-0079198 A | 7/2011 |
| KR | 10-2011-0112696 A | 10/2011 |
| KR | 10-2014-0072682 A | 6/2014 |
| KR | 10-1413072 B1 | 6/2014 |
| KR | 10-2014-0115238 A | 9/2014 |
| KR | 10-2015-0034626 A | 4/2015 |
| KR | 10-1531616 B1 | 6/2015 |
| TW | 201240948 A1 | 10/2012 |
| TW | 201543148 A | 11/2015 |
| WO | WO 2008/094637 A2 | 8/2008 |
| WO | WO 2011/059457 A1 | 5/2011 |

OTHER PUBLICATIONS

International Search Report for PCT/KR2017/004956.
International Search Report for PCT/KR2017/006197.
U.S. Office action received in co pending U.S. Appl. No. 16/308,871 dated Mar. 9, 2021.

\* cited by examiner

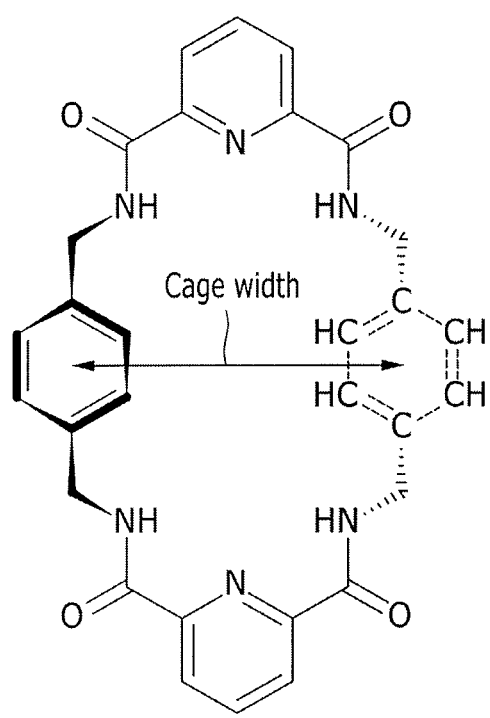

COMPOUND, CORE-SHELL DYE, PHOTOSENSITIVE RESIN COMPOSITION INCLUDING THE SAME, AND COLOR FILTER

CROSS REFERENCE TO RELATED APPLICATIONS

This is the U.S. national phase application based on PCT Application No. PCT/KR2017/004956, filed May 12, 2017, which is based on Korean Patent Application No. 10-2016-0123227, filed Sep. 26, 2016, the entire contents of all of which are hereby incorporated by reference.

BACKGROUND OF THE INVENTION

(a) Field of the Invention

This disclosure relates to a novel compound, a core-shell dye, a photosensitive resin composition including the same, and a color filter manufactured using the same.

(b) Description of the Related Art

A liquid crystal display device among many kinds of displays has an advantage of lightness, thinness, low cost, low power consumption for operation, and improved adherence to an integrated circuit and has been more widely used for a laptop computer, a monitor, and a TV screen. The liquid crystal display device includes a lower substrate on which a black matrix, a color filter, and an ITO pixel electrode are formed, and an upper substrate on which an active circuit portion including a liquid crystal layer, a thin film transistor, and a capacitor layer and an ITO pixel electrode are formed.

Color filters are formed in a pixel region by sequentially stacking a plurality of color filters (in general, formed of three primary colors such as red (R), green (G), and blue (B) in a predetermined order to form each pixel, and a black matrix layer is disposed in a predetermined pattern on a transparent substrate to form a boundary between the pixels.

The pigment dispersion method that is one of methods of forming a color filter provides a colored thin film by repeating a series of processes such as coating a photopolymerizable composition including a colorant on a transparent substrate including a black matrix, exposing a formed pattern to light, removing a non-exposed part with a solvent, and thermally curing the same.

A coloring photosensitive resin composition used for manufacturing a color filter according to the pigment dispersion method generally includes an alkali soluble resin, a photopolymerizable monomer, a photopolymerization initiator, an epoxy resin, a solvent, other additives, and the like. The pigment dispersion method is actively applied to manufacture an LCD of a mobile phone, a laptop, a monitor, and TV.

However, a photosensitive resin composition for a color filter for the pigment dispersion method has recently required improved performance as well as excellent pattern characteristics. Particularly, high color reproducibility and high luminance and high contrast ratio characteristics are urgently required. An image sensor is a part for photographing images in a portable phone camera or DSC (a digital still camera).

It may be classified as a charge-coupled device (CCD) image sensor and a complementary metal oxide semiconductor (CMOS) image sensor depending upon the manufacturing process and the application method.

A color imaging device for a charge-coupled device image sensor or a complementary metal oxide semiconductor image sensor includes color filters each having filter segments of mixing primary color of red, green, and blue, and the colors are separated.

A recent color filter mounted in the color imaging device has a pattern size of 2 μm or less, which is ¹⁄₁₀₀th to ¹⁄₂₀₀th of the pattern size of a conventional color filter pattern for LCDs.

Accordingly, increased resolution and decreased pattern residues are important factors for determining the performance of a device.

A color filter manufactured by using a conventional pigment-type photosensitive resin composition has a limit in luminance and a contrast ratio due to the size of pigment particles.

In addition, a color imaging device for an image sensor needs a smaller dispersion particle diameter for forming a fine pattern. In order to correspond to the requirements, an attempt to realize a color filter having improved luminance and a contrast ratio has been made by introducing a dye forming no particle instead of the pigment to prepare a photosensitive resin composition appropriate for the dye.

However, a dye has inferior durability such as light resistance and heat resistance, and the like to a pigment and thus luminance may be deteriorated.

SUMMARY OF THE INVENTION

An embodiment provides a novel compound having improved luminance and contrast ratio.

Another embodiment provides a core-shell dye including the novel compound.

Yet another embodiment provides a photosensitive resin composition including the novel compound or the core-shell dye.

Still another embodiment provides a color filter manufactured using the photosensitive resin composition.

An embodiment provides a compound represented by Chemical Formula 1.

[Chemical Formula 1]

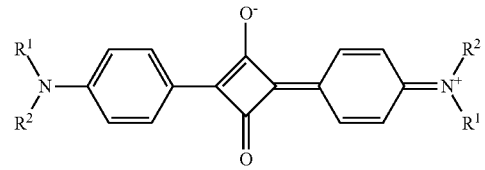

In Chemical Formula 1,
$R^1$ is a substituted or unsubstituted C3 to C20 cycloalkyl group or represented by Chemical Formula 2, and
$R^2$ is a substituted C6 to C20 aryl group,

[Chemical Formula 2]

wherein in Chemical Formula 2,
$R^3$ and $R^4$ are independently a substituted or unsubstituted C1 to C10 alkyl group.

$R^2$ may be a C6 to C20 aryl group substituted with a C1 to C10 alkyl group.

$R^2$ may be represented by Chemical Formula 3.

[Chemical Formula 3]

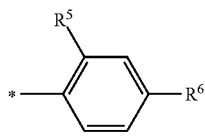

In Chemical Formula 3, $R^5$ and $R^6$ are independently a C1 to C7 alkyl group.

The compound represented by Chemical Formula 1 may be one selected from compounds represented by Chemical Formula 1-1 to Chemical Formula 1-7.

[Chemical Formula 1-1]

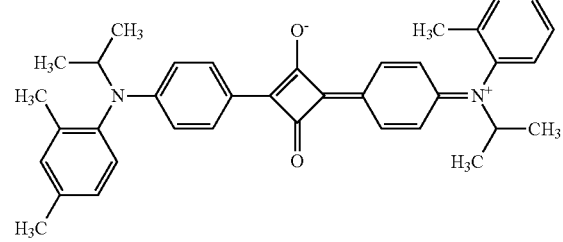

[Chemical Formula 1-2]

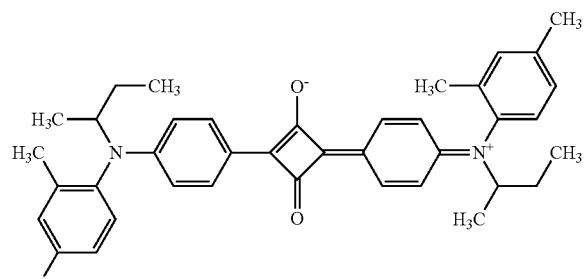

[Chemical Formula 1-3]

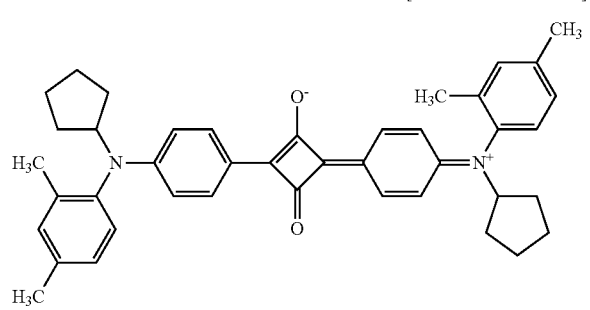

[Chemical Formula 1-4]

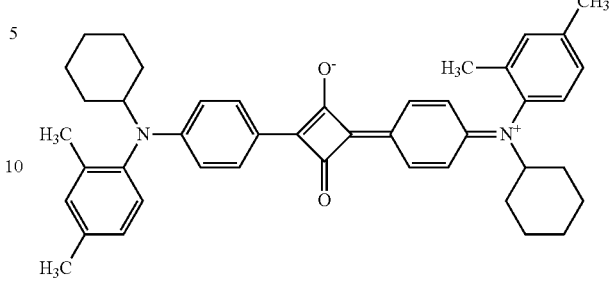

[Chemical Formula 1-5]

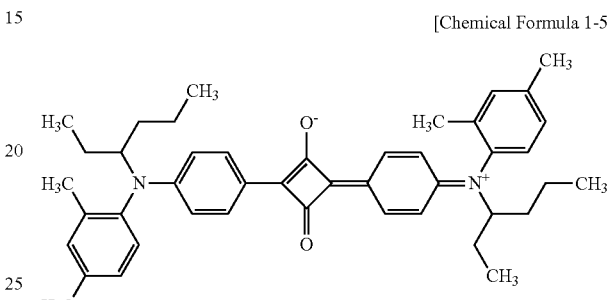

[Chemical Formula 1-6]

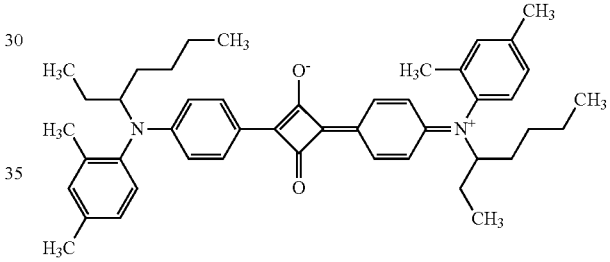

[Chemical Formula 1-7]

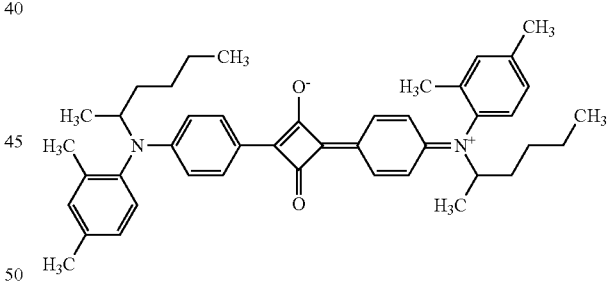

Another embodiment provides a core-shell dye including a core including the compound represented by Chemical Formula 1; and a shell surrounding the core.

The shell may be represented by Chemical Formula 4 or Chemical Formula 5.

[Chemical Formula 4]

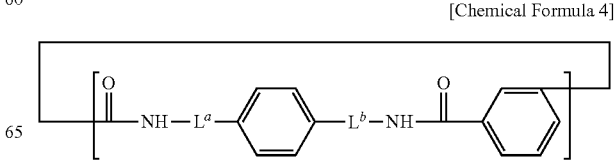

-continued

[Chemical Formula 5]

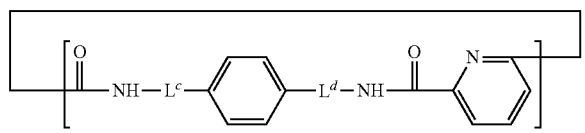

In Chemical Formula 4 and Chemical Formula 5, $L^a$ to $L^d$ are independently a single bond or a substituted or unsubstituted C1 to C10 alkylene group.

$L^a$ to $L^d$ may independently be a substituted or unsubstituted C1 to C10 alkylene group.

The shell may be represented by Chemical Formula 4-1 or Chemical Formula 5-1.

[Chemical Formula 4-1]

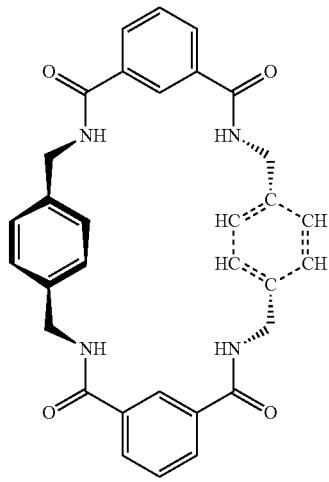

[Chemical Formula 5-1]

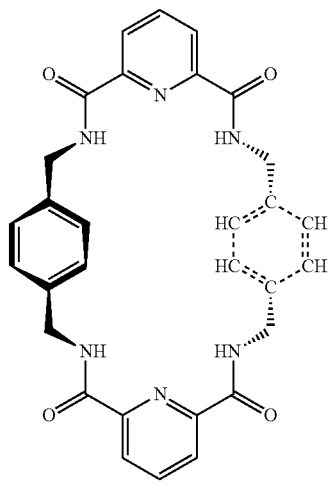

A cage width of the shell may range from 6.5 Å to 7.5 Å.

The core may have a length of 1 nm to 3 nm.

The core may have a maximum absorption peak in a wavelength of 530 nm to 680 nm.

The core-shell dye may be selected from compounds represented by Chemical Formula 6 to Chemical Formula 19.

[Chemical Formula 6]

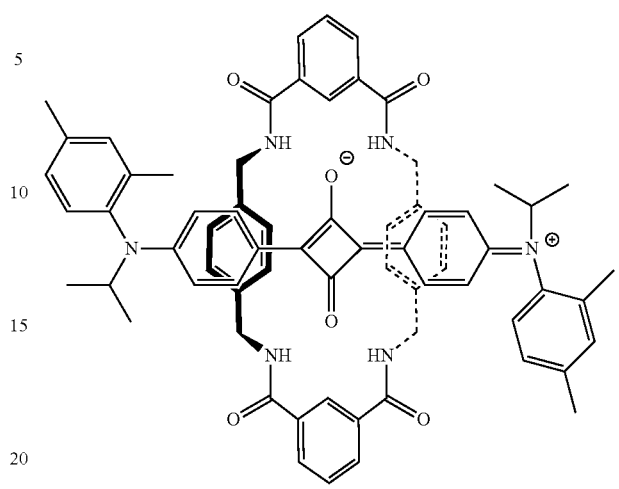

[Chemical Formula 7]

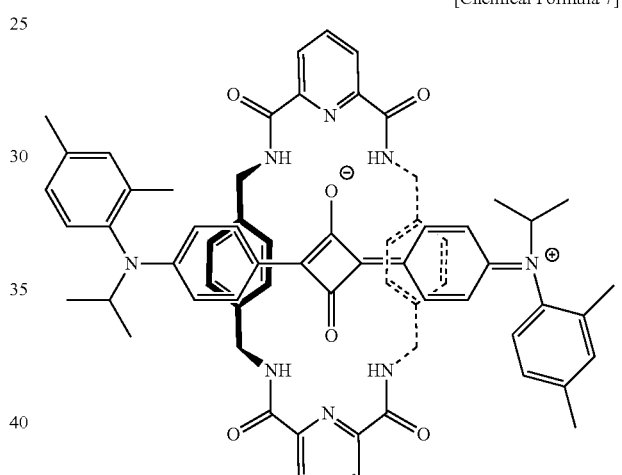

[Chemical Formula 8]

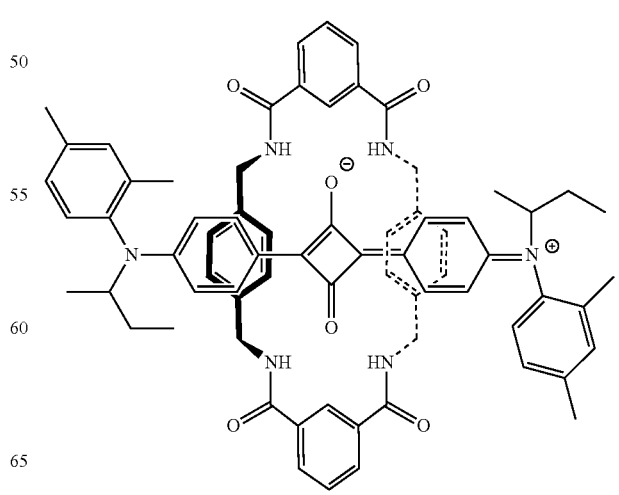

[Chemical Formula 9]
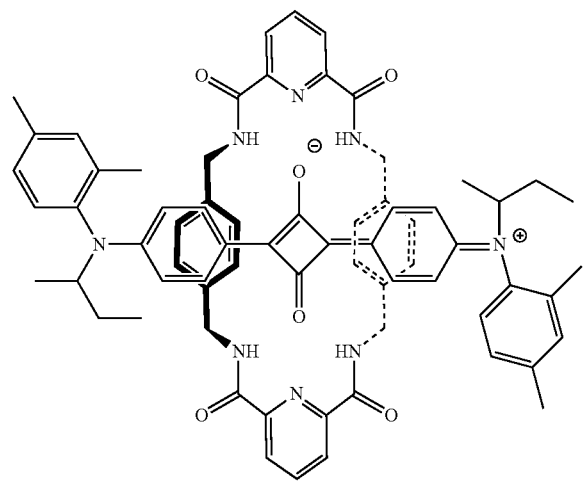
[Chemical Formula 12]
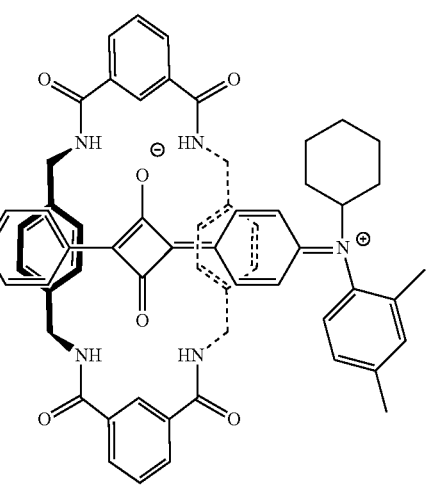
[Chemical Formula 10]
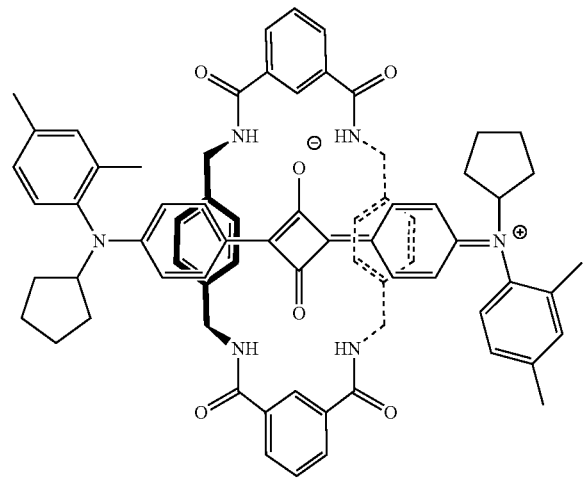
[Chemical Formula 13]
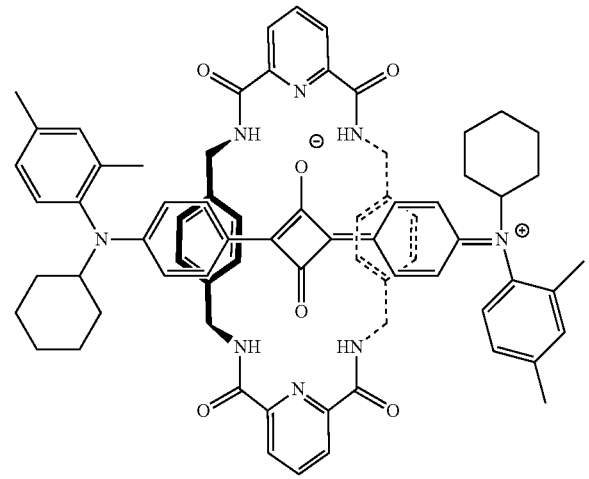
[Chemical Formula 11]
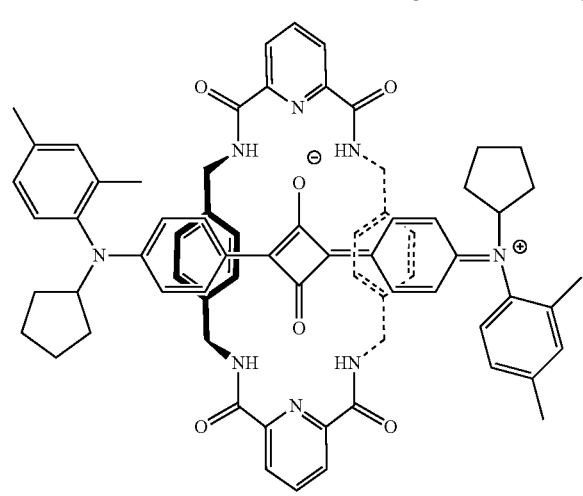
[Chemical Formula 14]
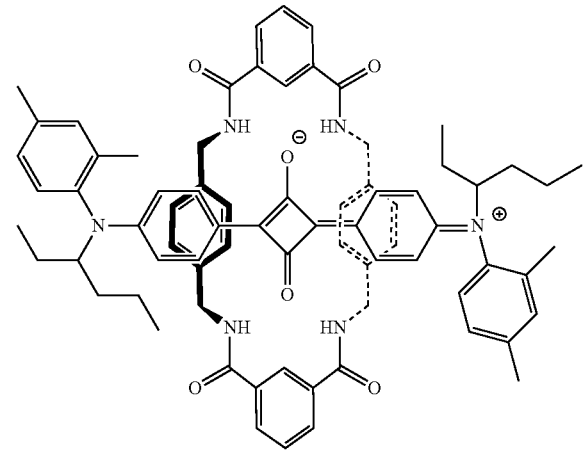

[Chemical Formula 15]

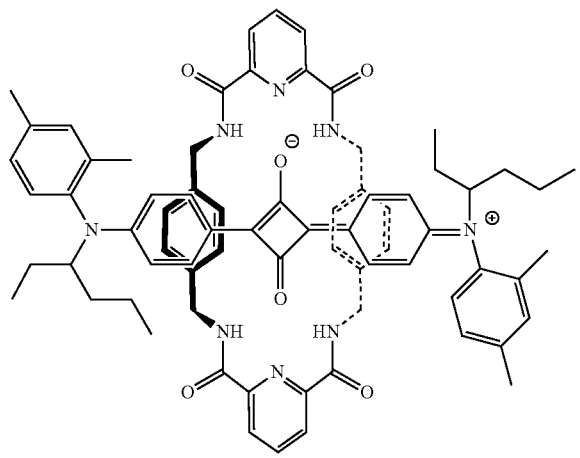

[Chemical Formula 16]

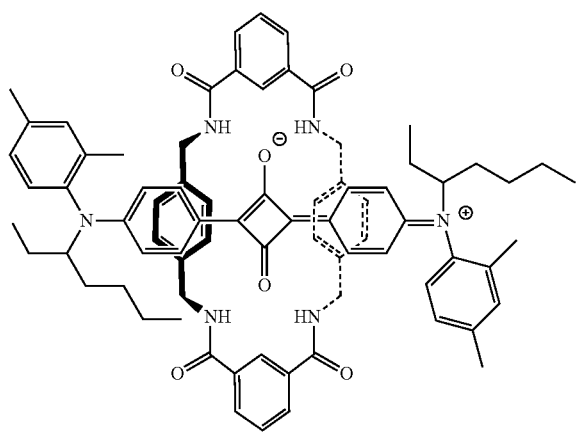

[Chemical Formula 17]

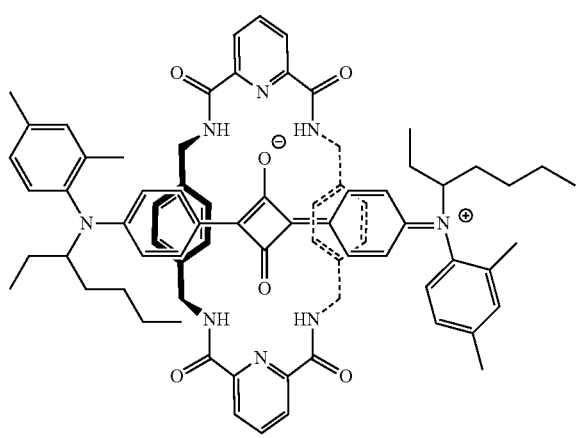

[Chemical Formula 18]

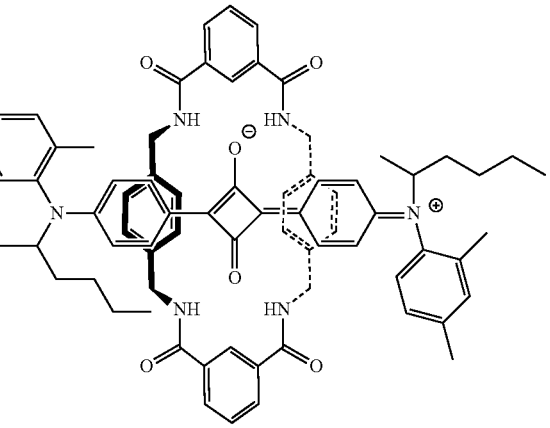

[Chemical Formula 19]

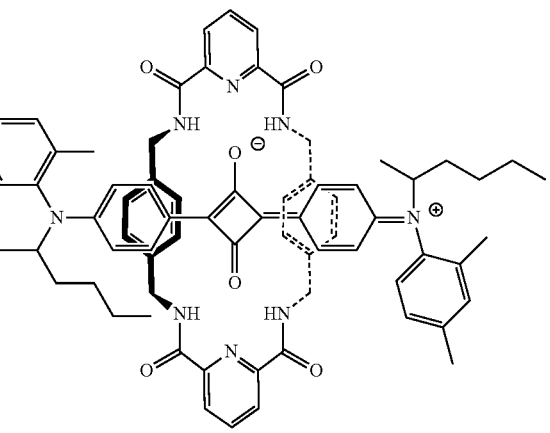

The core-shell dye may include the core and the shell in a mole ratio of 1:1.

The core-shell dye may be a green dye.

Another embodiment provides a photosensitive resin composition including the compound or the core-shell dye.

The photosensitive resin composition may further include a binder resin, a photopolymerizable monomer, a photopolymerization initiator, and a solvent.

The photosensitive resin composition may further include a pigment.

The photosensitive resin composition may include 0.5 wt % to 10 wt % of the compound or the core-shell dye; 0.1 wt % to 30 wt % of the binder resin; 0.1 wt % to 30 wt % of the photopolymerizable monomer; 0.1 wt % to 5 wt % of the photopolymerization initiator; and a balance amount of the solvent based on a total amount of the photosensitive resin composition.

The photosensitive resin composition may further include malonic acid, 3-amino-1,2-propanediol, a silane-based coupling agent including a vinyl group or a (meth)acryloxy group, a leveling agent, a surfactant, a radical polymerization initiator, or a combination thereof.

Another embodiment provides a color filter manufactured using the photosensitive resin composition.

Other embodiments of the present invention are included in the following detailed description.

The compound or the core-shell dye according to an embodiment realizes a color filter having improved luminance and contrast ratio.

BRIEF DESCRIPTION OF THE DRAWING

FIG. 1 is a view showing a cage width of a shell represented by Chemical Formula 5-1.

DETAILED DESCRIPTION

Hereinafter, embodiments of the present invention are described in detail. However, these embodiments are exemplary, the present invention is not limited thereto and the present invention is defined by the scope of claims.

In the present specification, when specific definition is not otherwise provided, "substituted" refers to replacement of at least one hydrogen atom of a compound by a substituent of a halogen atom (F, Cl, Br, or I), a hydroxy group, a C1 to C20 alkoxy group, a nitro group, a cyano group, an amine group, an imino group, an azido group, an amidino group, a hydrazino group, a hydrazono group, a carbonyl group, a carbamyl group, a thiol group, an ester group, an ether group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C3 to C20 cycloalkyl group, a C3 to C20 cycloalkenyl group, a C3 to C20 cycloalkynyl group, a C2 to C20 heterocycloalkyl group, a C2 to C20 heterocycloalkenyl group, a C2 to C20 heterocycloalkynyl group, or a combination thereof.

In the present specification, when specific definition is not otherwise provided, a "heterocycloalkyl group", a "heterocycloalkenyl group", a "heterocycloalkynyl group," and a "heterocycloalkylene group" refer to each cyclic compound of cycloalkyl, cycloalkenyl, cycloalkynyl, and cycloalkylene including at least one heteroatom of N, O, S, or P.

In the present specification, when specific definition is not otherwise provided, "(meth)acrylate" refers to both "acrylate" and "methacrylate".

In the present specification, when specific definition is not otherwise provided, the term "combination" refers to mixing or copolymerization.

In the present specification, when a definition is not otherwise provided, hydrogen is bonded at the position when a chemical bond is not drawn where supposed to be given.

In the present specification, when specific definition is not otherwise provided, "*" indicates a point where the same or different atom or chemical formula is linked.

A compound according to an embodiment is represented by Chemical Formula 1.

[Chemical Formula 1]

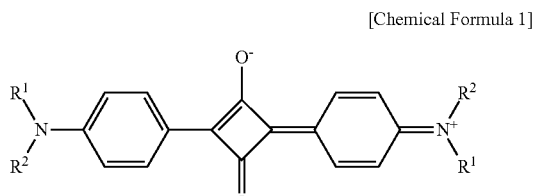

In Chemical Formula 1,
$R^1$ is a substituted or unsubstituted C3 to C20 cycloalkyl group or represented by Chemical Formula 2, and
$R^2$ is a substituted C6 to C20 aryl group,

[Chemical Formula 2]

wherein, in Chemical Formula 2,
$R^3$ and $R^4$ are independently a substituted or unsubstituted C1 to C10 alkyl group.
$R^1$ and $R^2$ may not be linked to form a fused ring.

The compound represented by Chemical Formula 1 has excellent green spectral characteristics and a high molar extinction coefficient and may be used as a green dye. However, the compound has insufficient durability compared with a pigment and thus may deteriorate luminance during a baking process after formed into a color resist. A compound according to an embodiment includes a branched alkyl functional group (represented by Chemical Formula 2) and a substituted aryl functional group (more specifically represented by Chemical Formula 3) which are different substituents and are symmetrical to each other, and thereby durability may be improved and a color filter having high luminance and a high contrast ratio may be realized.

For example, $R^2$ may be a C6 to C20 aryl group substituted with a C1 to C10 alkyl group.

For example, $R^2$ may be represented by Chemical Formula 3.

[Chemical Formula 3]

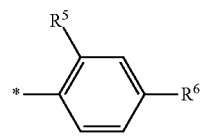

In Chemical Formula 3,
$R^5$ and $R^6$ are independently a C1 to C7 alkyl group.

When the compound represented by Chemical Formula 1 is used in a photosensitive resin composition (e.g., as a dye), solubility in a post-described solvent may be greater than or equal to 5, for example, range from 5 to 10. The solubility may be obtained by an amount (g) of the dye (compound) dissolved in 100 g of the solvent. When the compound (e.g., dye) has solubility within the range, compatibility and coloring properties with other components in the photosensitive resin composition, that is, post-described binder resin, photopolymerizable monomer, and photopolymerization initiator may be secured, and precipitation of the dye may be prevented.

The compound represented by Chemical Formula 1 may have excellent heat resistance. That is, a thermal decomposition temperature measured using a thermogravimetric analyzer (TGA) may greater than or equal to 200° C., for example, 200° C. to 300° C.

The compound represented by Chemical Formula 1 has three kinds of resonance structures as shown in the following diagram, but in the present specification, the compound having one kind of a resonance structure and represented by Chemical Formula 1 is shown for convenience. In other words, the compound represented by Chemical Formula 1 may have any one structure of the three resonance structures.

[Diagram]
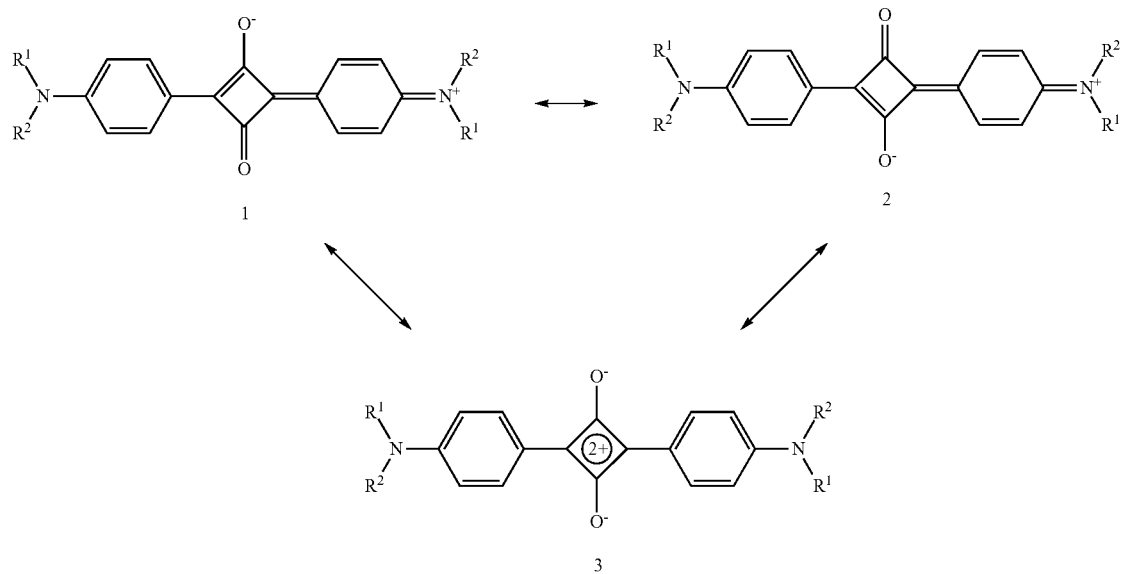
The compound represented by Chemical Formula 1 may be selected from compounds represented by Chemical Formula 1-1 to Chemical Formula 1-7.
[Chemical Formula 1-1]
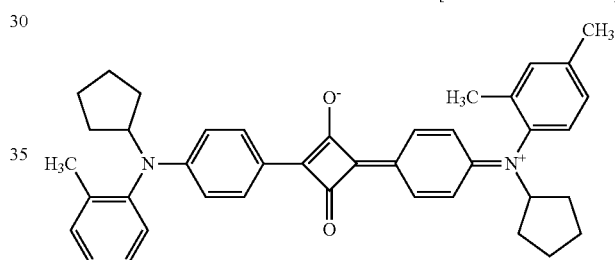
[Chemical Formula 1-2]
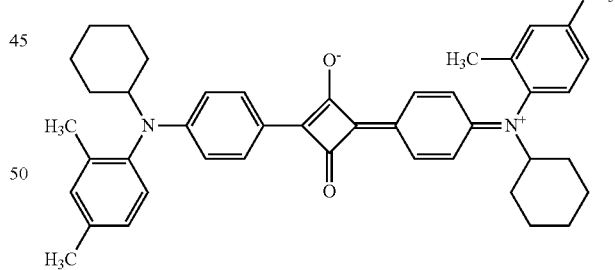
[Chemical Formula 1-3]
[Chemical Formula 1-4]
[Chemical Formula 1-5]
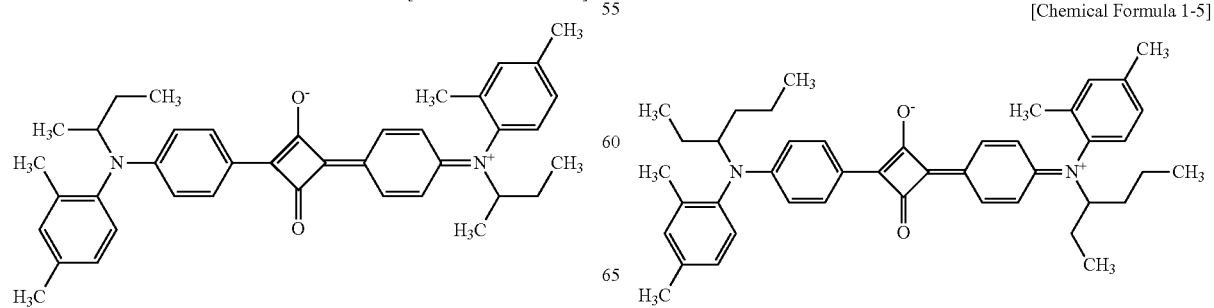

-continued

[Chemical Formula 1-6]

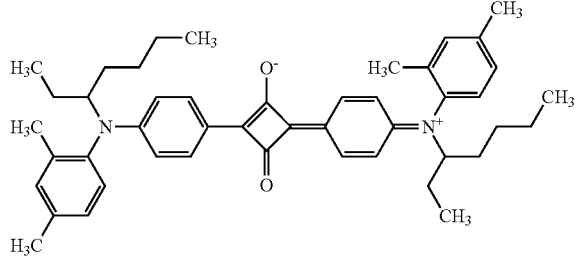

[Chemical Formula 1-7]

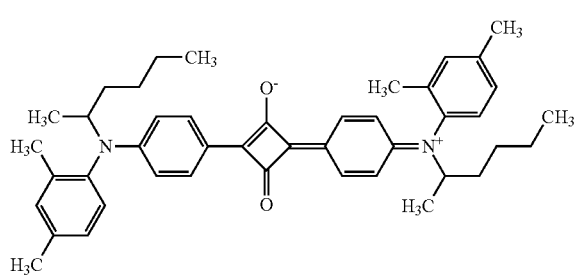

A core-shell dye according to another embodiment has a structure consisting of a core and a shell surrounding the core. The core includes the compound represented by Chemical Formula 1. Specifically, the shell may be a huge cyclic compound and the shell surrounds the compound represented by Chemical Formula 1 to form a coating layer.

In an embodiment, the compound represented by Chemical Formula 1 is surrounded by the shell corresponding to a huge cyclic compound, that is, the compound represented by Chemical Formula 1 is present inside the huge cycle, and thereby durability of the core-shell dye may be improved and a color filter having high luminance and a high contrast ratio may be realized.

A length of the compound represented by Chemical Formula 1 included in the core or composed of the core may be 1 nm to 3 nm, for example, 1.5 nm to 2 nm. When the compound represented by Chemical Formula 1 has a length within the range, a core-shell dye may easily have a structure that a shell surrounds a core. In other words, the compound represented by Chemical Formula 1 has a length within the range and thus may have a structure that the huge cyclic compound, that is, the shell surrounds the compound represented by Chemical Formula 1. When a compound having a length out of the range is used, the structure that the shell does not surround the core compound may not be obtained, and durability may not be improved.

The compound represented by Chemical Formula 1 included in the core or composed of the core may have a maximum absorption peak in a wavelength of 530 nm to 680 nm. The core-shell dye using the compound represented by Chemical Formula 1 having the spectral characteristics as a core is for example used as a green dye and thereby a photosensitive resin composition for a color filter having high luminance and high contrast ratio may be provided.

The shell surrounding the core including the compound represented by Chemical Formula 1 may be represented by Chemical Formula 4 or Chemical Formula 5.

[Chemical Formula 4]

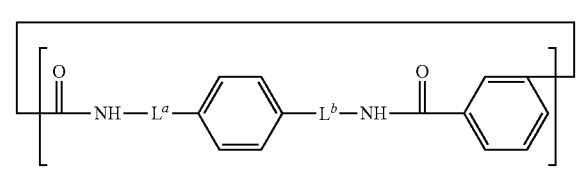

[Chemical Formula 5]

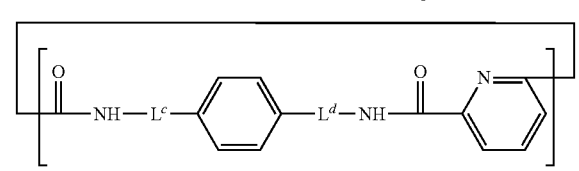

In Chemical Formula 4 and Chemical Formula 5, $L^a$ to $L^d$ are independently a single bond or a substituted or unsubstituted C1 to C10 alkylene group.

In Chemical Formula 4 or Chemical Formula 5, $L^a$ to $L^d$ may independently be a substituted or unsubstituted C1 to C10 alkylene group. In this case, a structure having improved solubility where a shell surrounds the core including the compound represented by Chemical Formula 1 is easily formed.

For example, the core-shell dye according to an embodiment includes a non-covalent bond, that is, a hydrogen bond between an oxygen atom of the compound represented by Chemical Formula 1 and a nitrogen atom of the shell represented by Chemical Formula 4 or Chemical Formula 5.

The shell may be for example represented by Chemical Formula 4-1 or Chemical Formula 5-1.

[Chemical Formula 4-1]

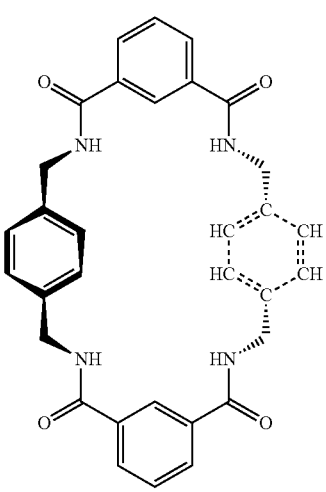

[Chemical Formula 5-1]

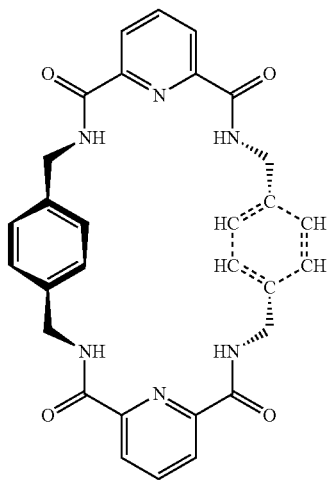

A cage width of the shell may range from 6.5 Å to 7.5 Å and a volume of the shell may range from 10 Å to 16 Å. The cage width in this disclosure refers to an internal distance of the shell, for example in a shell represented by Chemical Formula 4-1 or Chemical Formula 5-1, a distance between two different phenylene groups in which both methylene groups are linked (See FIG. 1). When the shell has a cage width within the range, a core-shell dye having a structure surrounding the core including the compound represented by Chemical Formula 1 may be obtained, and thus a color filter having improved durability and high luminance may be realized when the core-shell dye is added to a photosensitive resin composition.

The core-shell dye includes the core including the compound represented by Chemical Formula 1 and the shell in a mole ratio of 1:1. When the core and shell are present within the mole ratio, a coating layer (shell) surrounding the core including the compound represented by Chemical Formula 1 may be formed well.

For example, the core-shell dye may be selected from compounds represented by Chemical Formula 6 to Chemical Formula 19, but is not limited thereto.

[Chemical Formula 6]

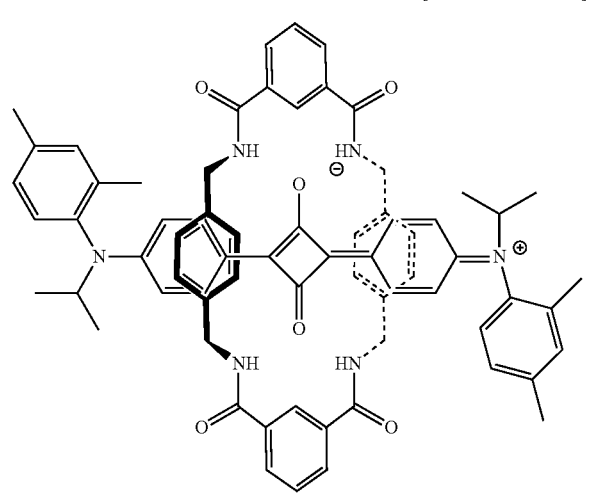

[Chemical Formula 7]

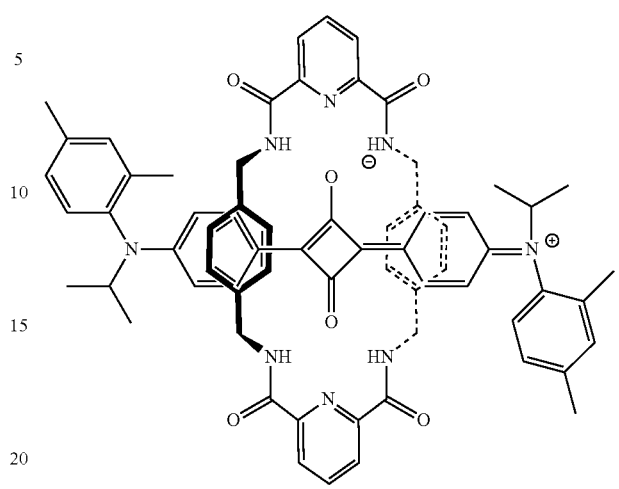

[Chemical Formula 8]

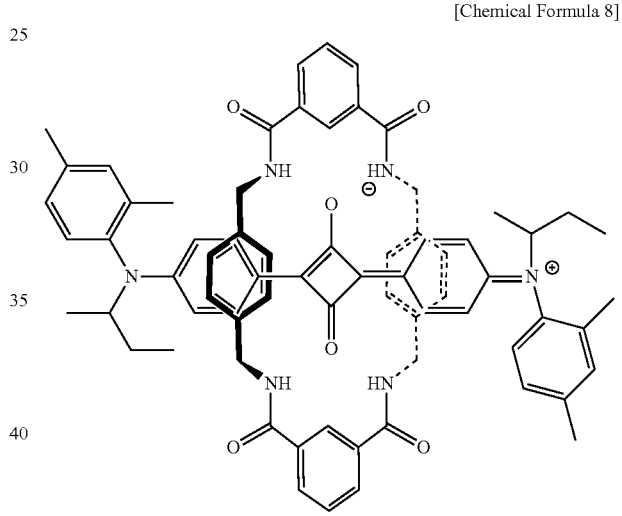

[Chemical Formula 9]

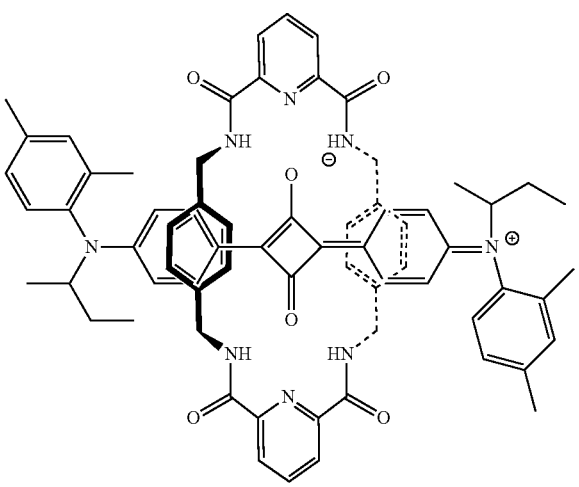

-continued
[Chemical Formula 10]
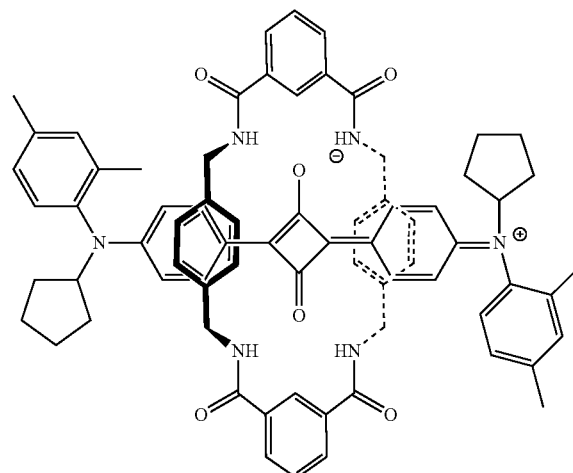
[Chemical Formula 11]
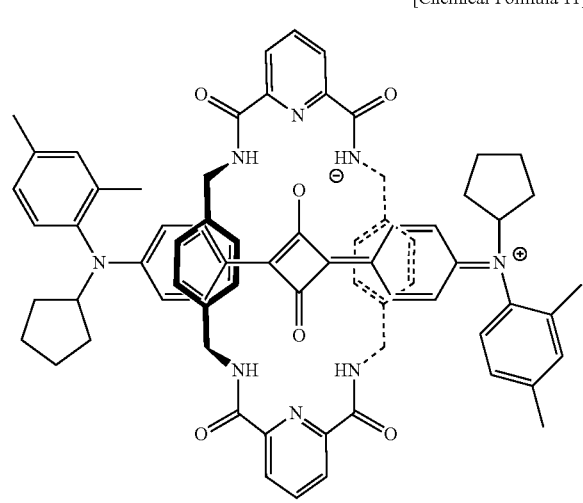
[Chemical Formula 12]
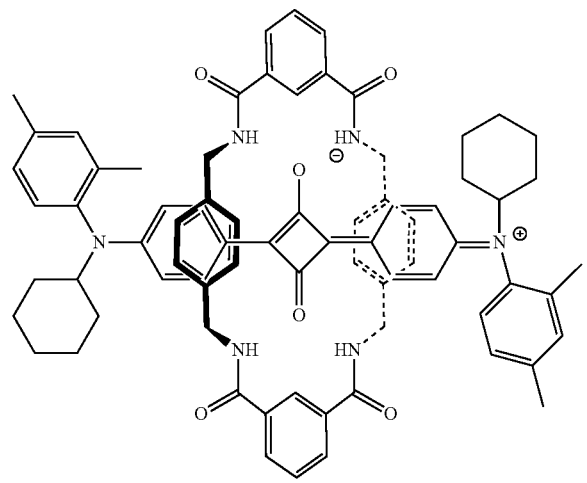
-continued
[Chemical Formula 13]
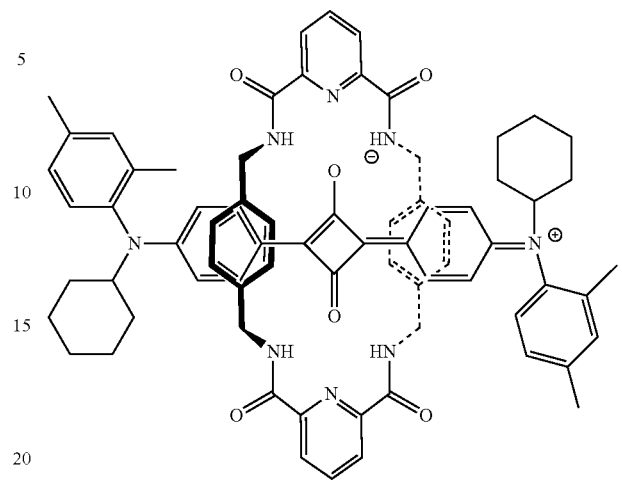
[Chemical Formula 14]
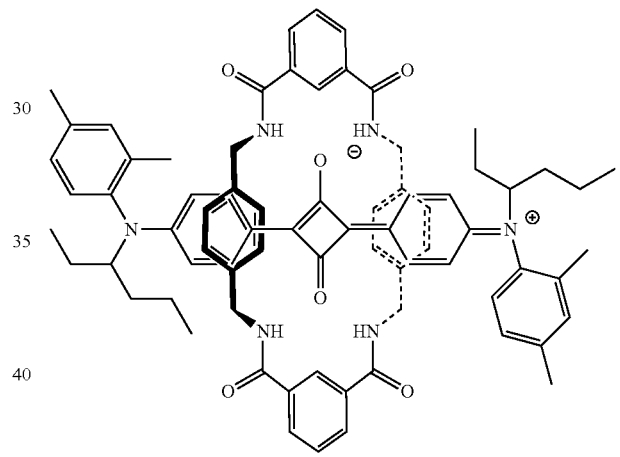
[Chemical Formula 15]
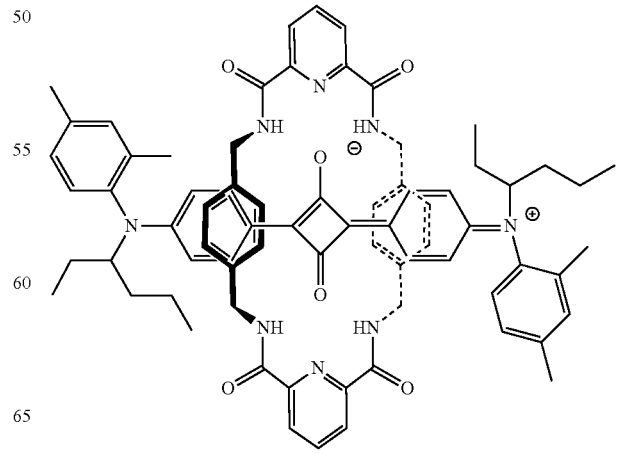

[Chemical Formula 16]

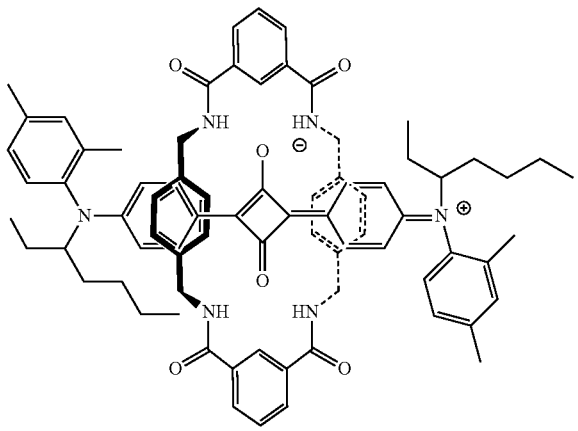

[Chemical Formula 17]

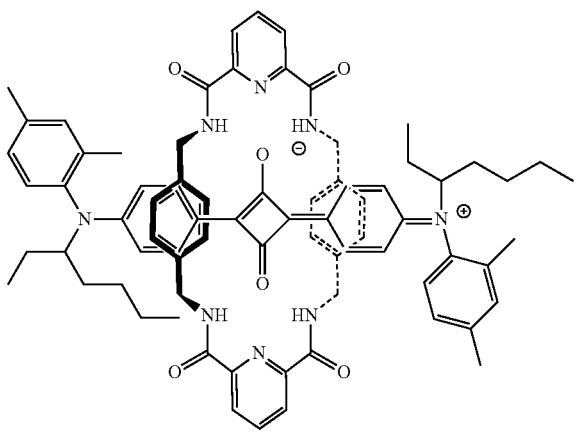

[Chemical Formula 18]

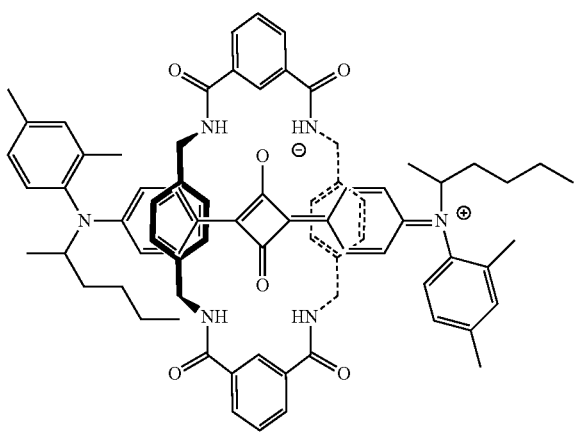

[Chemical Formula 19]

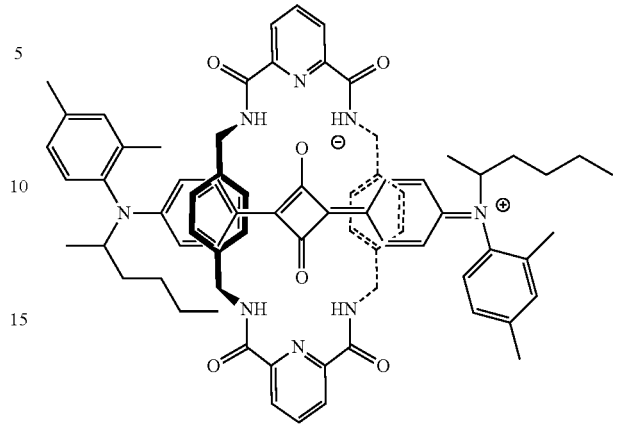

The core-shell dye may be used alone as a green dye and may be mixed with an auxiliary dye.

The auxiliary dye may be a triarylmethane-based dye, an anthraquinone-based dye, a benzylidene-based dye, a cyanine-based dye, phthalocyanine-based dye, an azaporphyrin-based dye, an indigo-based dye, a xanthene-based dye, and the like.

The core-shell dye may be mixed with a pigment.

The pigment may be a red pigment, a green pigment, a blue pigment, a yellow pigment, a black pigment, and the like.

Examples of the red pigment may be C.I. red pigment 254, C.I. red pigment 255, C.I. red pigment 264, C.I. red pigment 270, C.I. red pigment 272, C.I. red pigment 177, C.I. red pigment 89, and the like. Examples of the green pigment may be C.I. green pigment 36, C.I. green pigment 7, C.I. green pigment 58, C.I. green pigment 59, and the like. Examples of the blue pigment may be a copper phthalocyanine pigment such as C.I. blue pigment 15:6, C.I. blue pigment 15, C.I. blue pigment 15:1, C.I. blue pigment 15:2, C.I. blue pigment 15:3, C.I. blue pigment 15:4, C.I. blue pigment 15:5, C.I. blue pigment 16, and the like. Examples of the yellow pigment may be an isoindoline-based pigment such as C.I. yellow pigment 139, a quinophthalone-based pigment such as C.I. yellow pigment 138, a nickel complex pigment such as C.I. yellow pigment 150, and the like. Examples of the black pigment may be aniline black, perylene black, titanium black, carbon black, and the like. The pigment may be used alone or as a mixture of two or more and is not limited thereto.

The pigment may be included in the photosensitive resin composition for a color filter in a pigment dispersion liquid state. The pigment dispersion liquid may consist of the pigment and a solvent, a dispersing agent, a dispersing resin, and the like.

The solvent may be ethylene glycol acetate, ethyl cellosolve, propylene glycol methyl ether acetate, ethyl lactate, polyethylene glycol, cyclohexanone, propylene glycol methyl ether, and the like, and preferably propylene glycol methyl ether acetate.

The dispersing agent helps uniform dispersion of the pigment, and may include a non-ionic, anionic, or cationic dispersing agent. Specific examples may be polyalkylene glycol or esters thereof, polyoxy alkylene, polyhydric alcohol ester alkylene oxide addition products, alcohol alkylene oxide addition products, sulfonate esters, sulfonate salts, carboxylate esters, carboxylate salts, alkyl amide alkylene oxide addition products, alkyl amines, and may be used alone or as a mixture of two or more.

The dispersing resin may be an acryl-based resin including a carboxyl group, and improves stability of the pigment dispersion liquid and pattern properties of a pixel.

When the core-shell dye and the pigment are mixed, the core-shell dye and the pigment may be mixed in a weight ratio of 1:9 to 9:1 and specifically in a weight ratio of 3:7 to 7:3. When they are mixed within the weight ratio range, high luminance and contrast ratios may be obtained while color characteristics are maintained.

According to another embodiment, a photosensitive resin composition including the compound represented by Chemical Formula 1 or the core-shell dye is provided.

The photosensitive resin composition includes (A) a colorant (the compound represented by Chemical Formula 1 or the core-shell dye), (B) a binder resin, (C) a photopolymerizable monomer, (D) a photopolymerization initiator, and (E) a solvent.

Hereinafter, each component is specifically described.

(A) Colorant

The colorant may include the compound represented by Chemical Formula 1 and/or the core-shell dye and the compound represented by Chemical Formula 1 and/or the core-shell dye are described above.

The colorant may further include a pigment in addition to the compound represented by Chemical Formula 1 and/or the core-shell dye and the pigment is described above.

The compound represented by Chemical Formula 1 and/or the core-shell dye may be included in an amount of 0.5 wt % to 10 wt %, for example 0.5 wt % to 5 wt % based on a total amount of the photosensitive resin composition for a color filter. When the compound represented by Chemical Formula 1 and/or the core-shell dye is used within the range, high luminance and a high contrast ratio at a desirable color coordinate may be realized.

(B) Binder Resin

The binder resin is a copolymer of a first ethylenic unsaturated monomer and a second ethylenic unsaturated monomer that is copolymerizable therewith, and is resin including at least one acryl-based repeating unit.

The first ethylenic unsaturated monomer is an ethylenic unsaturated monomer including at least one carboxyl group. Examples of the monomer include (meth)acrylic acid, maleic acid, itaconic acid, fumaric acid, or a combination thereof.

The first ethylenic unsaturated monomer may be included in an amount of 5 wt % to 50 wt %, for example 10 wt % to 40 wt % based on a total amount of the alkali soluble resin.

The second ethylenic unsaturated monomer may be an aromatic vinyl compound such as styrene, α-methylstyrene, vinyl toluene, vinylbenzylmethylether and the like; an unsaturated carboxylate ester compound such as methyl (meth)acrylate, ethyl(meth)acrylate, butyl(meth)acrylate, 2-hydroxyethyl(meth)acrylate, 2-hydroxy butyl(meth)acrylate, benzyl(meth)acrylate, cyclohexyl(meth)acrylate, phenyl(meth)acrylate, and the like; an unsaturated amino alkyl carboxylate ester compound such as 2-aminoethyl(meth) acrylate, 2-dimethylaminoethyl(meth)acrylate, and the like; a carboxylic acid vinyl ester compound such as vinyl acetate, vinyl benzoate, and the like; an unsaturated glycidyl carboxylate ester compound such as glycidyl(meth)acrylate, and the like; a vinyl cyanide compound such as (meth) acrylonitrile and the like; an unsaturated amide compound such as (meth)acrylamide, and the like; and the like, and may be used alone or as a mixture of two or more.

Specific examples of the binder resin may be a methacrylic acid/benzylmethacrylate copolymer, a methacrylic acid/benzylmethacrylate/styrene copolymer, a methacrylic acid/benzylmethacrylate/2-hydroxyethylmethacrylate copolymer, a methacrylic acid/benzylmethacrylate/styrene/2-hydroxyethylmethacrylate copolymer and the like, but are not limited thereto. These may be used alone or as a mixture of two or more.

A weight average molecular weight of the binder resin may be 3,000 g/mol to 150,000 g/mol, for example 5,000 g/mol to 50,000 g/mol, for example 20,000 g/mol to 30,000 g/mol. When the binder resin has a weight average molecular weight within the range, close contacting properties with a substrate and physicochemical properties are improved and viscosity is appropriate.

An acid value of the binder resin may be 15 mgKOH/g to 60 mgKOH/g, for example 20 mgKOH/g to 50 mgKOH/g. When the binder resin has an acid value within the range, excellent resolution of a pixel may be obtained.

The binder resin may be included in an amount of 0.1 wt % to 30 wt %, for example 5 wt % to 20 wt % based on a total amount the photosensitive resin composition. When the binder resin is included within the above range, developability may be improved and excellent surface smoothness may be improved due to improved cross-linking during the manufacture of a color filter.

(C) Photopolymerizable Monomer

The photopolymerizable monomer may be a mono-functional or multi-functional ester of (meth)acrylic acid including at least one ethylenic unsaturated double bond.

The photopolymerizable monomer may cause sufficient polymerization during exposure in a pattern-forming process and form a pattern having excellent heat resistance, light resistance, and chemical resistance due to the ethylenic unsaturated double bond.

Specific examples of the photopolymerizable monomer may be ethylene glycol di(meth)acrylate, diethylene glycol di(meth)acrylate, triethylene glycol di(meth)acrylate, propylene glycol di(meth)acrylate, neopentyl glycol di(meth) acrylate, 1,4-butanediol di(meth)acrylate, 1,6-hexanediol di(meth)acrylate, bisphenol A di(meth)acrylate, pentaerythritol di(meth)acrylate, pentaerythritol tri(meth)acrylate, pentaerythritol tetra(meth)acrylate, pentaerythritol hexa(meth) acrylate, dipentaerythritol di(meth)acrylate, dipentaerythritol tri(meth)acrylate, dipentaerythritol penta (meth)acrylate, dipentaerythritol hexa(meth)acrylate, bisphenol A epoxy(meth)acrylate, ethylene glycol monomethylether (meth)acrylate, trimethylol propane tri(meth)acrylate, tris(meth)acryloyloxyethyl phosphate, novolacepoxy (meth) acrylate, and the like.

Commercially available examples of the photopolymerizable monomer may be as follows. The mono-functional (meth)acrylic acid ester may include Aronix M101®, M-111®, M-114® (Toagosei Chemistry Industry Co., Ltd.); KAYARAD TC-110S®, TC-120S® (Nippon Kayaku Co., Ltd.); V-158®, V-2311® (Osaka Organic Chemical Ind., Ltd.), and the like. Examples of a difunctional (meth)acrylic acid ester may include Aronix M-210°, M-240®, M-6200® (Toagosei Chemistry Industry Co., Ltd.), KAYARAD HDDA®, HX-220®, R-604® (Nippon Kayaku Co., Ltd.), V-260®, V-312®, V-335 HP® (Osaka Organic Chemical Ind., Ltd.), and the like. Examples of a tri-functional (meth) acrylic acid ester may include Aronix M-309®, M-400®, M-405®, M-450®, M-7100®, M-8030®, M-8060° (Toagosei Chemistry Industry Co., Ltd.); KAYARAD TMPTA®, DPCA-20®, DPCA-30®, DPCA-60®, DPCA-120® (Nippon Kayaku Co., Ltd.); V-295®, V-300®, V-360®, V-GPT®, V-3PA®, V-400® (Osaka Yuki Kayaku Kogyo Co. Ltd.), and the like. These may be used alone or as a mixture of two or more.

The photopolymerizable monomer may be treated with acid anhydride to improve developability.

The photopolymerizable monomer may be included in an amount of 0.1 wt % to 30 wt %, for example 5 wt % to 20 wt % based on a total amount of the photosensitive resin composition. When the photopolymerizable monomer is included within the range, pattern characteristic and developability during manufacture of a color filter may be improved.

(D) Photopolymerization Initiator

The photopolymerization initiator may be an acetophenone-based compound, a benzophenone-based compound, a thioxanthone-based compound, a benzoin-based compound, a triazine-based compound, an oxime-based compound, and the like.

Examples of the acetophenone-based compound may be 2,2'-diethoxy acetophenone, 2,2'-dibutoxy acetophenone, 2-hydroxy-2-methylpropinophenone, p-t-butyltrichloro acetophenone, p-t-butyldichloro acetophenone, 4-chloro acetophenone, 2,2'-dichloro-4-phenoxy acetophenone, 2-methyl-1-(4-(methylthio)phenyl)-2-morpholinopropan-1-one, 2-benzyl-2-dimethylamino-1-(4-morpholinophenyl)-butan-1-one, and the like.

Examples of the benzophenone-based compound may be benzophenone, benzoyl benzoate, benzoyl methyl benzoate, 4-phenyl benzophenone, hydroxy benzophenone, acrylated benzophenone, 4,4'-bis(dimethyl amino)benzophenone, 4,4'-bis(diethylamino)benzophenone, 4,4'-dimethylamino-benzophenone, 4,4'-dichlorobenzophenone, 3,3'-dimethyl-2-methoxybenzophenone, and the like.

Examples of the thioxanthone-based compound may be thioxanthone, 2-methylthioxanthone, isopropyl thioxanthone, 2,4-diethyl thioxanthone, 2,4-diisopropyl thioxanthone, 2-chlorothioxanthone, and the like.

Examples of the benzoin-based compound may be benzoin, benzoin methyl ether, benzoin ethyl ether, benzoin isopropyl ether, benzoin isobutyl ether, benzyldimethylketal, and the like.

Examples of the triazine-based compound may be 2,4,6-trichloro-s-triazine, 2-phenyl 4,6-bis(trichloromethyl)-s-triazine, 2-(3',4'-dimethoxystyryl)-4,6-bis(trichloromethyl)-s-triazine, 2-(4'-methoxynaphthyl)-4,6-bis(trichloromethyl)-s-triazine, 2-(p-methoxyphenyl)-4,6-bis(trichloromethyl)-s-triazine, 2-(p-tolyl)-4,6-bis(trichloro methyl)-s-triazine, 2-biphenyl 4,6-bis(trichloro methyl)-s-triazine, bis(trichloromethyl)-6-styryl-s-triazine, 2-(naphthol-yl)-4,6-bis(trichloromethyl)-s-triazine, 2-(4-methoxynaphthol-yl)-4,6-bis(trichloromethyl)-s-triazine, 2-4-trichloromethyl (piperonyl)-6-triazine, 2-4-trichloromethyl (4'-methoxystyryl)-6-triazine, and the like.

Examples of the oxime-based compound may be 2-(o-benzoyloxime)-1-[4-(phenylthio)phenyl]-1,2-octandione, 1-(o-acetyloxime)-1-[9-ethyl-6-(2-methylbenzoyl)-9H-carbazol-3-yl]ethanone, and the like.

The photopolymerization initiator may further include a carbazole-based compound, a diketone-based compound, a sulfonium borate-based compound, a diazo-based compound, an imidazole-based compound, a biimidazole-based compound, a fluorene-based compound, and the like in addition to the compounds.

The photopolymerization initiator may be included in an amount of 0.1 wt % to 5 wt %, for example 1 wt % to 3 wt % based on a total amount of the photosensitive resin composition. When the photopolymerization initiator is included within the range, the composition may be sufficiently photopolymerized when exposed to light during the pattern-forming process for preparing a color filter, accomplishing excellent sensitivity and improving transmittance.

(E) Solvent

The solvent is not particularly limited and specifically for example, alcohols such as methanol, ethanol, and the like; ethers such as dichloroethyl ether, n-butyl ether, diisoamyl ether, methylphenyl ether, tetrahydrofuran, and the like; glycol ethers such as ethylene glycol methylether, ethylene glycol ethylether, propylene glycol methylether and the like; shellosolve acetates such as methyl shellosolve acetate, ethyl shellosolve acetate, diethyl shellosolve acetate, and the like; carbitols such as methylethyl carbitol, diethyl carbitol, diethylene glycol monomethylether, diethylene glycol monoethylether, diethylene glycol dimethylether, diethylene glycol methylethylether, diethylene glycol diethylether, and the like; propylene glycol alkylether acetates such as propylene glycol methylether acetate, propylene glycol propylether acetate, and the like; aromatic hydrocarbons such as toluene, xylene, and the like; ketones such as methylethylketone, cyclohexanone, 4-hydroxy-4-methyl-2-pentanone, methyl-n-propylketone, methyl-n-butylketone, methyl-n-amylketone, 2-heptanone and the like; saturated aliphatic monocarboxylic acid alkyl esters such as ethyl acetate, n-butyl acetate, isobutyl acetate, and the like; lactic acid alkyl esters such as methyl lactate, ethyl lactate, and the like; hydroxyacetic acid alkyl esters such as methyl hydroxyacetate, ethyl hydroxyacetate, butyl hydroxyacetate, and the like; acetic acid alkoxyalkyl esters such as methoxymethyl acetate, methoxyethyl acetate, methoxybutyl acetate, ethoxymethyl acetate, ethoxyethyl acetate, and the like; 3-hydroxypropionic acid alkyl esters such as methyl 3-hydroxypropionate, ethyl 3-hydroxypropionate, and the like; 3-alkoxypropionic acid alkyl esters such as methyl 3-methoxypropionate, ethyl 3-methoxypropionate, ethyl 3-ethoxypropionate, methyl 3-ethoxypropionate, and the like; 2-hydroxypropionic acid alkyl esters such as methyl 2-hydroxypropionate, ethyl 2-hydroxypropionate, propyl 2-hydroxypropionate, and the like; 2-alkoxypropionic acid alkyl esters such as methyl 2-methoxypropionate, ethyl 2-methoxypropionate, ethyl 2-ethoxypropionate, methyl 2-ethoxypropionate, and the like; 2-hydroxy-2-methylpropionic acid alkyl esters such as methyl 2-hydroxy-2-methylpropionate, ethyl 2-hydroxy-2-methylpropionate, and the like; 2-alkoxy-2-methylpropionic acid alkyl esters such as methyl 2-methoxy-2-methylpropionate, ethyl 2-ethoxy-2-methylpropionate, and the like; esters such as 2-hydroxyethyl propionate, 2-hydroxy-2-methylethyl propionate, hydroxyethyl acetate, methyl 2-hydroxy-3-methylbutanoate, and the like; or ketonate esters such as ethyl pyruvate, and the like, and additionally N-methylformamide, N,N-dimethyl formamide, N-methylformanilide, N-methylacetamide, N,N-dimethyl acetamide, N-methylpyrrolidone, dimethylsulfoxide, benzylethylether, dihexylether, acetylacetone, isophorone, caproic acid, caprylic acid, 1-octanol, 1-nonanol, benzylalcohol, benzyl acetate, ethyl benzoate, diethyl oxalate, diethyl maleate, γ-butyrolactone, ethylene carbonate, propylene carbonate, phenyl shellosolve acetate, and the like, which may be used alone or as a mixture of two or more.

Considering miscibility and reactivity, the solvent may desirably be ketones such as cyclohexanone, and the like; glycol ethers such as ethylene glycol monoethyl ether, and the like; ethylene glycol alkylether acetates such as ethyl shellosolve acetate, and the like; esters such as 2-hydroxyethyl propionate, and the like; diethylene glycols such as diethylene glycol monomethyl ether, and the like; propylene glycol alkylether acetates such as propylene glycol monomethylether acetate, propylene glycol propylether acetate, and the like.

The solvent is used in a balance amount, and specifically 20 wt % to 90 wt % based on a total amount of the photosensitive resin composition. The photosensitive resin composition for a color filter has a coating property, and may maintain excellent flatness of a film having a thickness of 3 μm or greater.

(F) Other Additives

The photosensitive resin composition may further include an additive such as malonic acid; 3-amino-1,2-propanediol; a silane-based coupling agent including a vinyl group or a (meth)acryloxy group; a leveling agent; a fluorine-based surfactant; a radical polymerization initiator, and the like in order to prevent stains or spots during the coating, to adjust leveling, or to prevent pattern residue due to non-development.

In addition, the photosensitive resin composition may further include an additive such as an epoxy compound, and the like in order to improve a close contacting property with a substrate.

Examples of the epoxy compound may be a phenol novolac epoxy compound, a tetramethyl biphenyl epoxy compound, a bisphenol A epoxy compound, an alicyclic epoxy compound, or a combination thereof.

An amount of the additive may be controlled according to desirable properties.

Another embodiment provides a color filter manufactured using the photosensitive resin composition is provided. A method of manufacturing the color filter is as follows.

The photosensitive resin composition for a color filter is coated on a bare glass substrate, or on a glass substrate on which $SiN_x$ is coated in a thickness of 500 Å to 1500 Å as a protective layer using an appropriate method of spin-coating, slit-coating, and the like to have a thickness of 3.1 μm to 3.4 μm. After the coating, light is irradiated to form a pattern required for a color filter. After irradiation, the coated layer is treated with an alkali developing solution, and a non-radiated region of the coated layer may be dissolved, forming a pattern for an image color filter. This process is repeated depending on the necessary number of R, G, and B colors, fabricating a color filter having a desired pattern.

In addition, the image pattern acquired by the development is cured through heat treatment, actinic ray radiation, or the like, resultantly improving crack resistance, solvent resistance, and the like.

Hereinafter, the present invention is preferably in more detail with reference to examples. These examples, however, are not in any sense to be interpreted as limiting the scope of the invention.

Intermediate Synthesis Example 1: Synthesis of Intermediate A 2,4-dimethyldiphenylamine (10 mol), 2-iodopropane (10 mol), and sodium hydride (10 mol) were put in N,N-dimethyl formamide, and the mixture was heated up to 80° C. and stirred for 24 hours. Ethyl acetate was added to the solution, and the obtained mixture is twice washed to extract an organic layer. The extracted organic layer was distilled under a reduced pressure and separated through column chromatography to obtain Intermediate A.

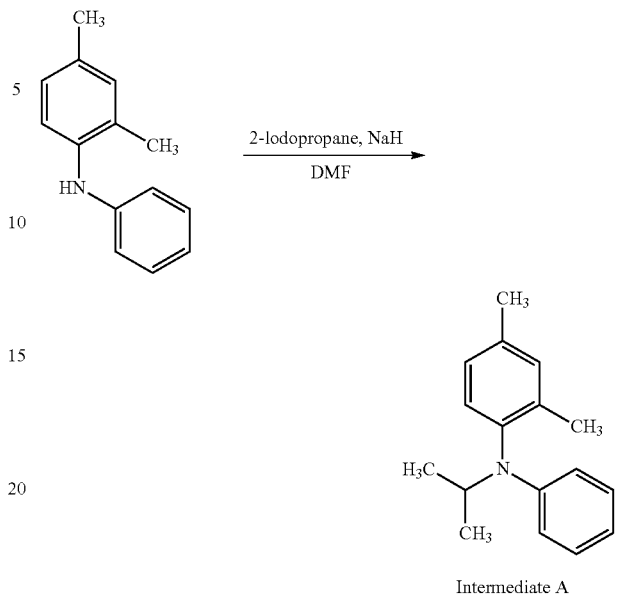

Maldi-tof MS: 239.36 m/z

Intermediate Synthesis Example 2: Synthesis of Intermediate B 2,4-dimethyldiphenylamine (10 mol), 2-iodobutane (10 mol), and sodium hydride (10 mol) were put in N,N-dimethyl formamide, and the mixture was heated up to 80° C. and stirred for 24 hours. Ethyl acetate was added thereto, and the obtained mixture was twice washed to extract an organic layer. The extracted organic layer was distilled under a reduced pressure and separated through column chromatography to obtain Intermediate B.

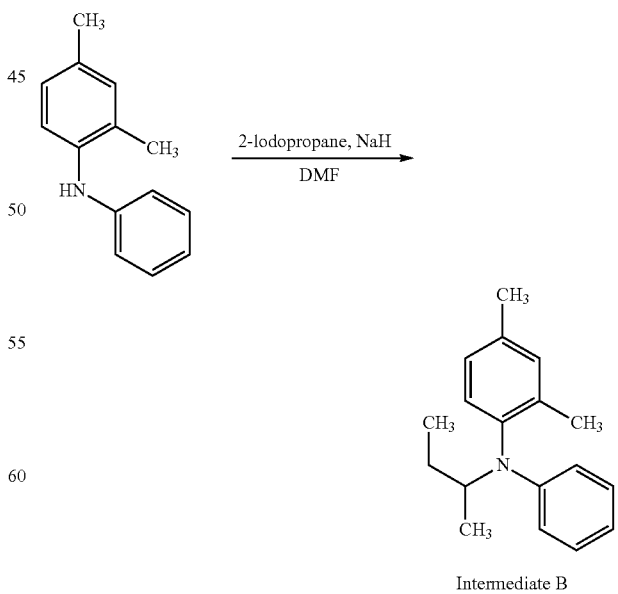

Maldi-tof MS: 253.39 m/z

Intermediate Synthesis Example 3: Synthesis of Intermediate C 2,4-dimethyldiphenylamine (10 mol), bromocyclopentane (10 mol), and sodium hydride (10 mol) were put in N,N-dimethyl formamide, and the mixture was heated up to 80° C. and stirred for 24 hours. Ethyl acetate was added thereto, and the obtained mixture was twice washed to extract an organic layer. The extracted organic layer was distilled under a reduced pressure and separated through column chromatography to obtain Intermediate C.

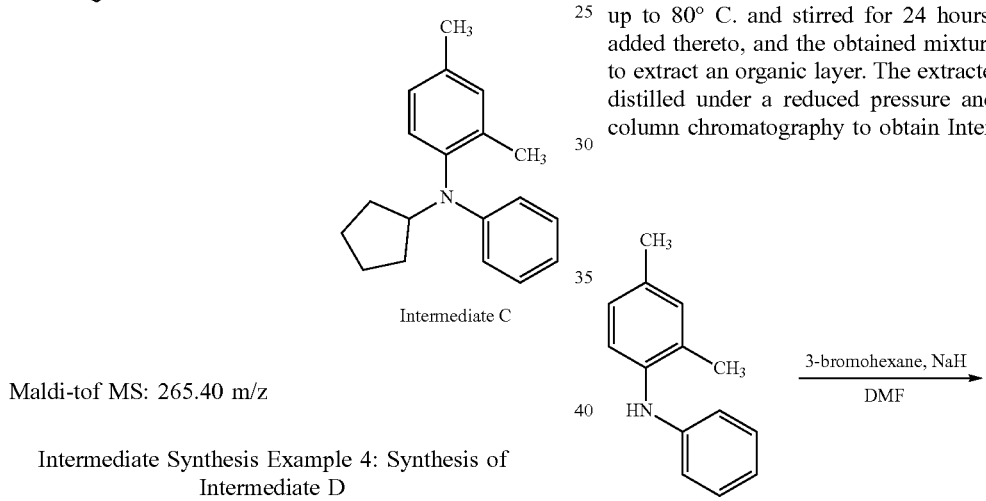

Intermediate C

Maldi-tof MS: 265.40 m/z

Intermediate Synthesis Example 4: Synthesis of Intermediate D 2,4-dimethyldiphenylamine (10 mol), bromocyclohexane (10 mol), and sodium hydride (10 mol) were put in N,N-dimethyl formamide, and the mixture was heated up to 80° C. and stirred for 24 hours. Ethyl acetate was added thereto, and the obtained mixture was twice washed to extract an organic layer. The extracted organic layer was distilled under a reduced pressure and separated through column chromatography to obtain Intermediate D.

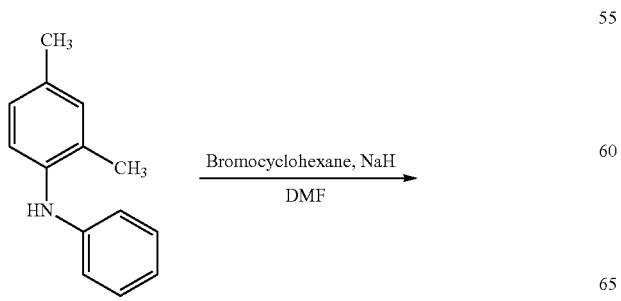

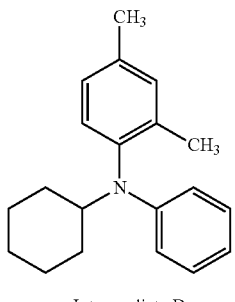

Intermediate D

Maldi-tof MS: 279.43 m/z

Intermediate Synthesis Example 5: Synthesis of Intermediate E 2,4-dimethyldiphenylamine (10 mol), 3-bromohexane (10 mol), and sodium hydride (10 mol) were put in N,N-dimethyl formamide, and the obtained mixture was heated up to 80° C. and stirred for 24 hours. Ethyl acetate was added thereto, and the obtained mixture was twice washed to extract an organic layer. The extracted organic layer was distilled under a reduced pressure and separated through column chromatography to obtain Intermediate E.

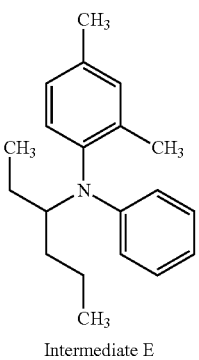

Intermediate E

Maldi-tof MS: 281.44 m/z

Intermediate Synthesis Example 6: Synthesis of Intermediate F 2,4-dimethyldiphenylamine (10 mol), 3-bromoheptane (10 mol), and sodium hydride (10 mol) were put in N,N-dimethyl formamide, and the mixture was heated up to 80° C. and stirred for 24 hours. Ethyl acetate was added thereto, and the obtained mixture was twice washed to extract an organic layer. The extracted organic layer was distilled under a reduced pressure and separated through column chromatography to obtain Intermediate F.

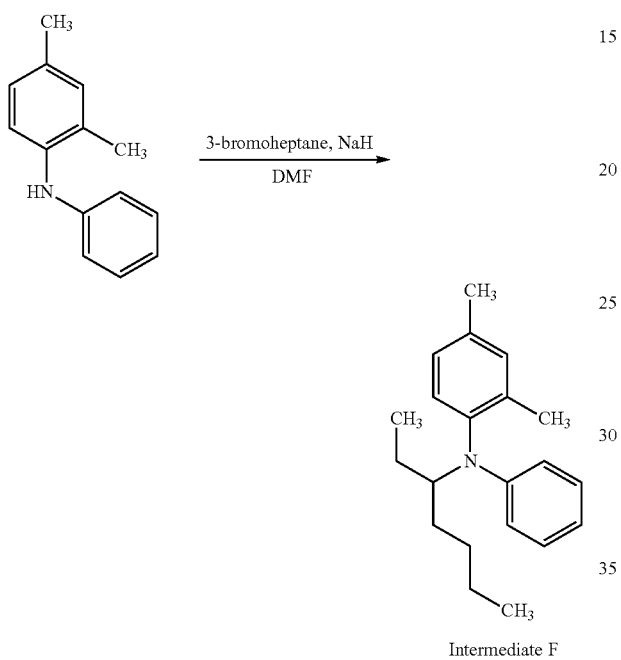

Intermediate F

Maldi-tof MS: 295.47 m/z

Intermediate Synthesis Example 7: Synthesis of Intermediate G 2,4-dimethyldiphenylamine (10 mol), 2-bromohexane (10 mol), and sodium hydride (10 mol) were put in N,N-dimethyl formamide, and the mixture was heated up to 80° C. and stirred for 24 hours. Ethyl acetate was added thereto, and the obtained mixture was twice washed to extract an organic layer. The extracted organic layer was distilled under a reduced pressure and separated through column chromatography to obtain Intermediate G.

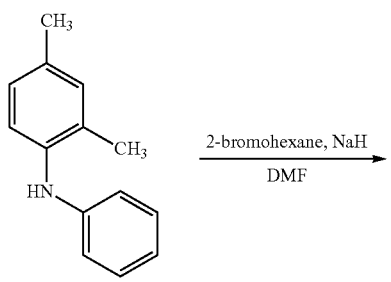

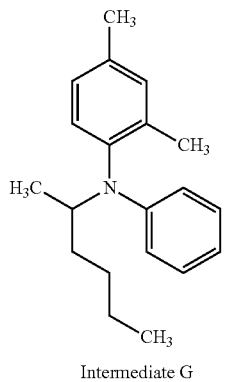

Intermediate G

Maldi-tof MS: 281.44 m/z

Synthesis Example 1: Synthesis of Compound Represented by Chemical Formula 1-1

Intermediate A (60 mmol) and 3,4-dihydroxy-3-cyclobutene-1,2-dione (30 mmol) were added to toluene (200 mL) and butanol (200 mL), and water generated by refluxing the obtained mixture was removed with a Dean-stark distillator. After stirred for 12 hours, a green product therefrom was distilled under a reduced pressure and purified through column chromatography to synthesize a compound represented by Chemical Formula 1-1.

[Chemical Formula 1-1]

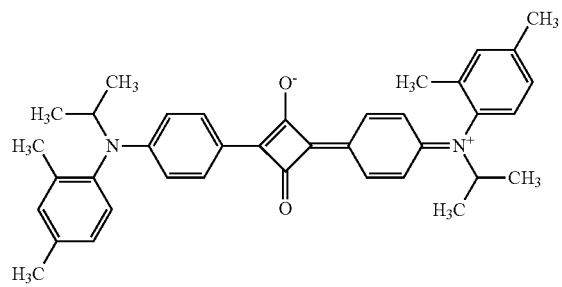

Maldi-tof MS: 556.75 m/z

Synthesis Example 2: Synthesis of Compound Represented by Chemical Formula 1-2

Intermediate B (60 mmol) and 3,4-dihydroxy-3-cyclobutene-1,2-dione (30 mmol) were added to toluene (200 mL) and butanol (200 mL), and water generated by refluxing the mixture was removed with a Dean-stark distillator. After stirred for 12 hours, a green product therefrom was distilled under a reduced pressure and purified through column chromatography to synthesize a compound represented by Chemical Formula 1-2.

[Chemical Formula 1-2]

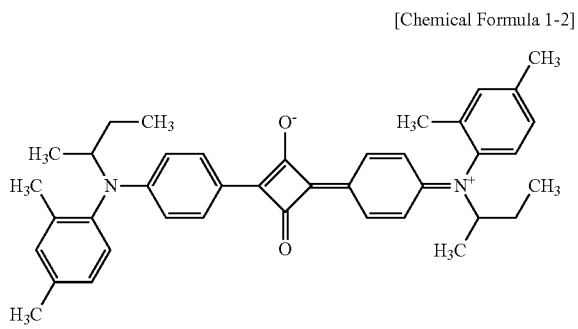 [SMILES: CCC(C)N(c1ccc(C2=C([O-])C(=C3C=CC(=[N+](c4ccc(C)cc4C)C(C)CC)C=C3)C2=O)cc1)c1ccc(C)cc1C]

Maldi-tof MS: 584.80 m/z

Synthesis Example 3: Synthesis of Compound Represented by Chemical Formula 1-3

Intermediate C (60 mmol) and 3,4-dihydroxy-3-cyclobutene-1,2-dione (30 mmol) were added to toluene (200 mL) and butanol (200 mL), and water generated by refluxing the mixture was removed with a Dean-stark distillator. After stirred for 12 hours, a green product therefrom was distilled under a reduced pressure and purified through column chromatography to synthesize a compound represented by Chemical Formula 1-3.

[Chemical Formula 1-3]

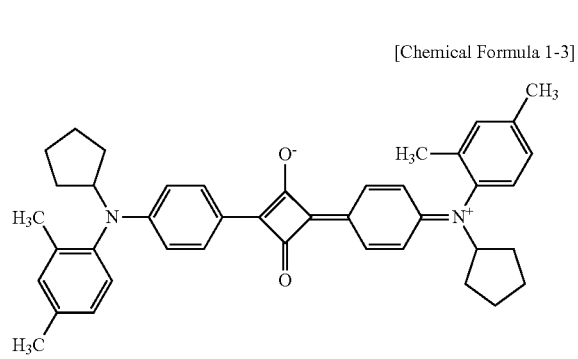 [SMILES: Cc1ccc(N(c2ccc(C3=C([O-])C(=C4C=CC(=[N+](c5ccc(C)cc5C)C5CCCC5)C=C4)C3=O)cc2)C2CCCC2)c(C)c1]

Maldi-tof MS: 608.83 m/z

Synthesis Example 4: Synthesis of Compound Represented by Chemical Formula 1-4

Intermediate D (60 mmol) and 3,4-dihydroxy-3-cyclobutene-1,2-dione (30 mmol) were added to toluene (200 mL) and butanol (200 mL), and water generated by refluxing the mixture was removed with a Dean-stark distillator. After stirred for 12 hours, a green product therefrom was distilled under a reduced pressure and purified through column chromatography to synthesize a compound represented by Chemical Formula 1-4.

[Chemical Formula 1-4]

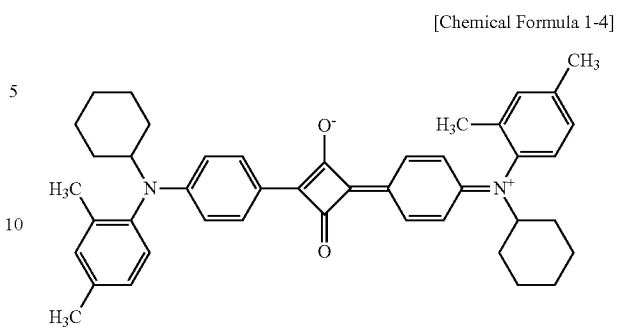

Maldi-tof MS: 636.88 m/z

Synthesis Example 5: Synthesis of Compound Represented by Chemical Formula 1-5

Intermediate E (60 mmol) and 3,4-dihydroxy-3-cyclobutene-1,2-dione (30 mmol) were added to toluene (200 mL) and butanol (200 mL), and water generated by refluxing the mixture was removed with a Dean-stark distillator. After stirred for 12 hours, a green product therefrom was distilled under a reduced pressure and purified through column chromatography to synthesize a compound represented by Chemical Formula 1-5.

[Chemical Formula 1-5]

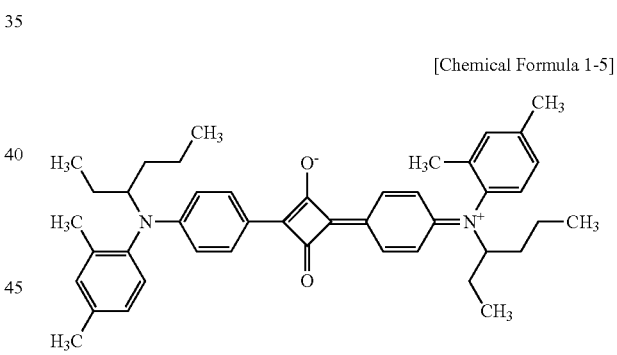

Maldi-tof MS: 640.91 m/z

Synthesis Example 6: Synthesis of Compound Represented by Chemical Formula 1-6

Intermediate F (60 mmol) and 3,4-dihydroxy-3-cyclobutene-1,2-dione (30 mmol) were added to toluene (200 mL) and butanol (200 mL), and water generated by refluxing the mixture was removed with a Dean-stark distillator. After stirred for 12 hours, a green product therefrom was distilled under a reduced pressure and purified through column chromatography to obtain a compound represented by Chemical Formula 1-6.

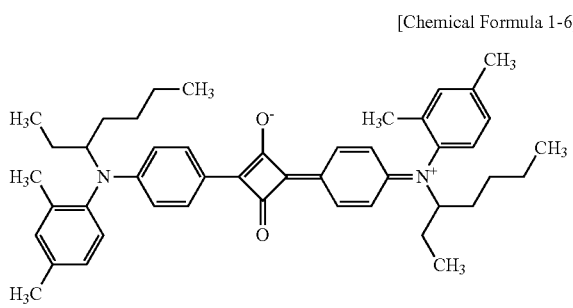 [SMILES: CCCCC(CC)N(c1ccc(C2=C([O-])C(=C3C=CC(=[N+](c4ccc(C)cc4C)C(CC)CCCC)C=C3)C2=O)cc1)c1ccc(C)cc1C]

Maldi-tof MS: 668.97 m/z

Synthesis Example 7: Synthesis of Compound Represented by Chemical Formula 1-7

Intermediate G (60 mmol) and 3,4-dihydroxy-3-cyclobutene-1,2-dione (30 mmol) were added to toluene (200 mL) and butanol (200 mL), and water generated by refluxing the mixture was removed with a Dean-stark distillator. After stirred for 12 hours, a green product therefrom was distilled under a reduced pressure and purified through column chromatography to synthesize a compound represented by Chemical Formula 1-7.

[Chemical Formula 1-7]

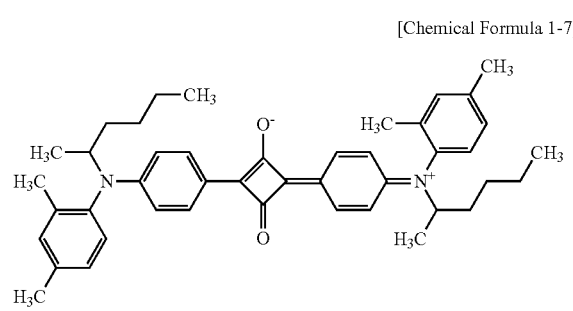 [SMILES: CCCCC(C)N(c1ccc(C2=C([O-])C(=C3C=CC(=[N+](c4ccc(C)cc4C)C(C)CCCC)C=C3)C2=O)cc1)c1ccc(C)cc1C]

Maldi-tof MS: 640.91 m/z

Synthesis Example 8: Synthesis of Core-Shell Dye Represented by Chemical Formula 6

The compound represented by Chemical Formula 1-1 (5 mmol) was dissolved in 600 mL of a chloroform solvent, and a solution obtained by dissolving isophthaloyl chloride (20 mmol) and p-xylylene diamine (20 mmol) in 60 mL of chloroform was added in a dropwise fashion thereto at room temperature for 5 hours. After 12 hours, the obtained mixture was distilled under a reduced pressure and separated through column chromatography to synthesize a core-shell dye represented by Chemical Formula 6.

[Chemical Formula 6]

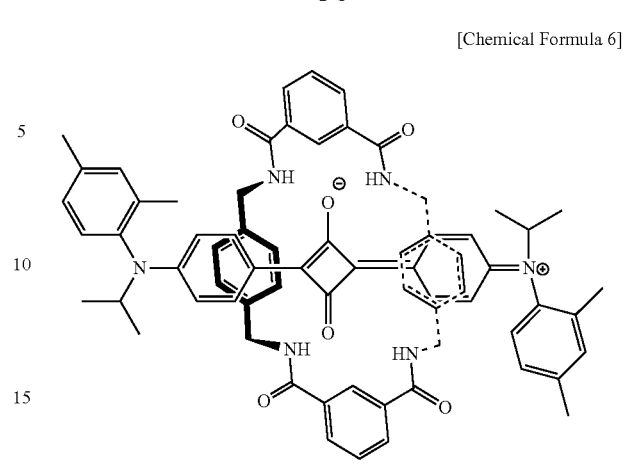

Maldi-tof MS: 1089.35 m/z

Synthesis Example 9: Synthesis of Core-Shell Dye Represented by Chemical Formula 7

The compound represented by Chemical Formula 1-1 (5 mmol) was dissolved in 600 mL of a chloroform solvent, and triethylamine (50 mmol) was added thereto. 2,6-pyridinedicarbonyl dichloride (20 mmol) and p-xylylene diamine (20 mmol) were dissolved in 60 mL of chloroform, and the obtained solution was added in a dropwise fashion to the above solution at room temperature for 5 hours. After 12 hours, the obtained mixture was distilled under a reduced pressure and separated through column chromatography to synthesize a core-shell dye represented by Chemical Formula 7.

[Chemical Formula 7]

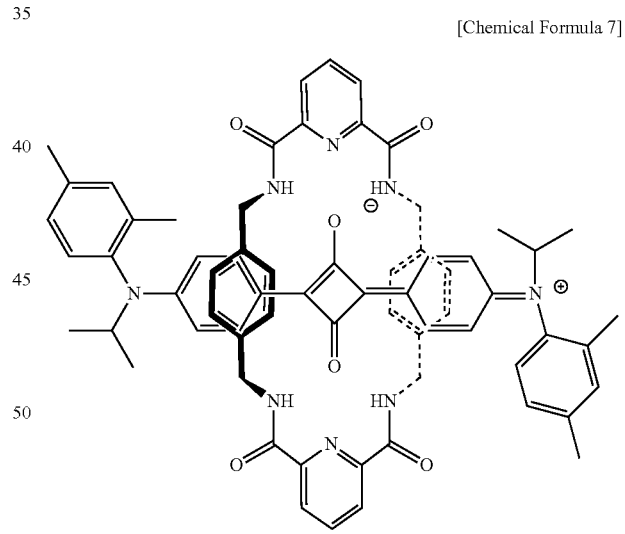

Maldi-tof MS: 1091.33 m/z

Synthesis Example 10: Synthesis of Core-Shell Dye Represented by Chemical Formula 8

The compound represented by Chemical Formula 1-2 (5 mmol) was dissolved in 600 mL of a chloroform solvent, and a solution obtained by dissolving Isophthaloyl chloride (20 mmol) and p-xylylene diamine (20 mmol) in 60 mL of chloroform was added in a dropwise fashion thereto at room temperature for 5 hours. After 12 hours, the obtained mixture was distilled under a reduced pressure and separated through column chromatography to synthesize a core-shell dye represented by Chemical Formula 8.

[Chemical Formula 8]

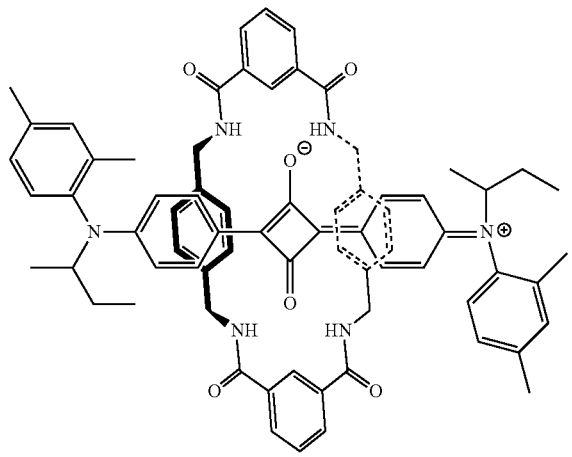

Maldi-tof MS: 1117.40 m/z

Synthesis Example 11: Synthesis of Core-Shell Dye Represented by Chemical Formula 9

The compound represented by Chemical Formula 1-2 (5 mmol) was dissolved in 600 mL of a chloroform solvent, and triethylamine (50 mmol) was added thereto. 2,6-pyridinedicarbonyl dichloride (20 mmol) and p-xylylene diamine (20 mmol) were dissolved in 60 mL of chloroform, and the obtained solution was added to the above solution at room temperature for 5 hours. After 12 hours, the obtained mixture was distilled under a reduced pressure and separated through column chromatography to synthesize a core-shell dye represented by Chemical Formula 9.

[Chemical Formula 9]

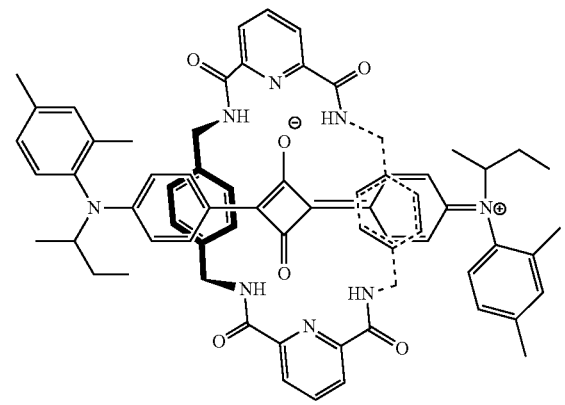

Maldi-tof MS: 1119.38 m/z

Synthesis Example 12: Synthesis of Core-Shell Dye Represented by Chemical Formula 10

The compound represented by Chemical Formula 1-3 (5 mmol) was dissolved in 600 mL of a chloroform solvent, and a solution obtained by dissolving isophthaloyl chloride (20 mmol) and p-xylylene diamine (20 mmol) in 60 mL of chloroform was added thereto in a dropwise fashion at room temperature for 5 hours. After 12 hours, the obtained mixture was distilled under a reduced pressure and separated through column chromatography to synthesize a core-shell dye represented by Chemical Formula 10.

[Chemical Formula 10]

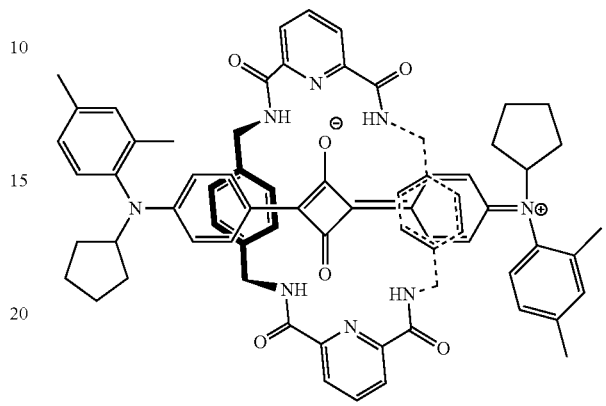

Maldi-tof MS: 1141.43 m/z

Synthesis Example 13: Synthesis of Core-Shell Dye Represented by Chemical Formula 11

The compound represented by Chemical Formula 1-3 (5 mmol) was dissolved in 600 mL of a chloroform solvent, and triethylamine (50 mmol) was added thereto. 2,6-pyridinedicarbonyl dichloride (20 mmol) and p-xylylene diamine (20 mmol) were dissolved in 60 mL of chloroform, and the obtained solution was added to the above solution in a dropwise fashion at room temperature for 5 hours. After 12 hours, the obtained mixture was distilled under a reduced pressure and separated through column chromatography to synthesize a core-shell dye represented by Chemical Formula 11.

[Chemical Formula 11]

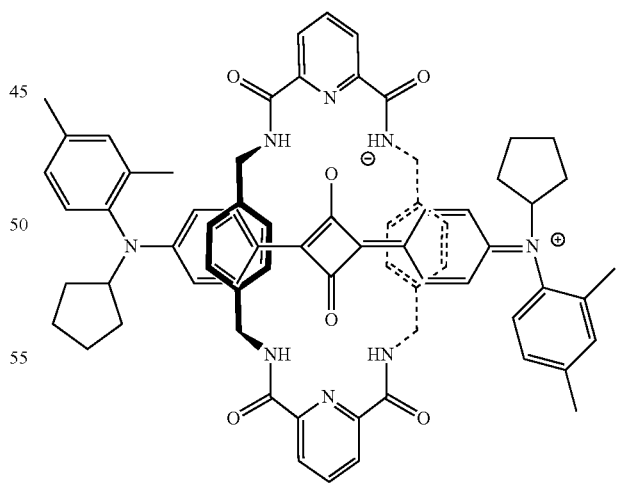

Maldi-tof MS: 1143.30 m/z

Synthesis Example 14: Synthesis of Core-Shell Dye Represented by Chemical Formula 12

The compound represented by Chemical Formula 1-4 (5 mmol) was dissolved in 600 mL of a chloroform solvent, and a solution obtained by dissolving isophthaloyl chloride (20 mmol) and p-xylylene diamine (20 mmol) in 60 mL of chloroform was added in a dropwise fashion thereto at room temperature for 5 hours. After 12 hours, the obtained mixture was distilled under a reduced pressure and separated through column chromatography to synthesize a core-shell dye represented by Chemical Formula 12.

[Chemical Formula 12]

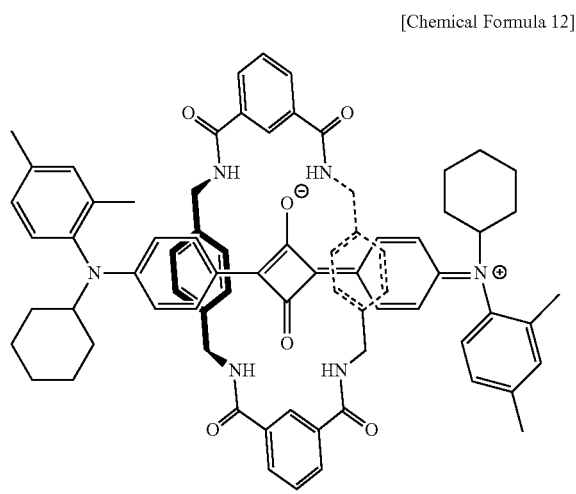

Maldi-tof MS: 1169.48 m/z

Synthesis Example 15: Synthesis of Core-Shell Dye Represented by Chemical Formula 13

The compound represented by Chemical Formula 1-4 (5 mmol) was dissolved in 600 mL of a chloroform solvent, and triethylamine (50 mmol) was added thereto. 2,6-pyridinedicarbonyl dichloride (20 mmol) and p-xylylene diamine (20 mmol) were dissolved in 60 mL of chloroform, and the obtained solution was added in a dropwise fashion to the above solution at room temperature for 5 hours. After 12 hours, the obtained mixture was distilled under a reduced pressure and separated through column chromatography to synthesize a core-shell dye represented by Chemical Formula 13.

[Chemical Formula 13]

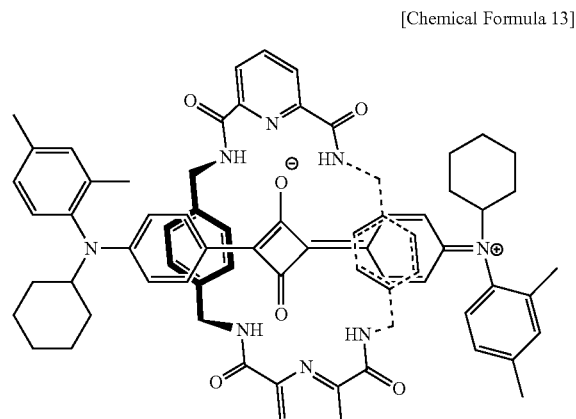

Maldi-tof MS: 1171.46 m/z

Synthesis Example 16: Synthesis of Core-Shell Dye Represented by Chemical Formula 14

The compound represented by Chemical Formula 1-5 (5 mmol) was dissolved in 600 mL of a chloroform solvent, and a solution obtained by dissolving isophthaloyl chloride (20 mmol) and p-xylylene diamine (20 mmol) in 60 mL of chloroform was added thereto in a dropwise fashion at room temperature for 5 hours. After 12 hours, the obtained mixture was distilled under a reduced pressure and separated through column chromatography to synthesize a core-shell dye represented by Chemical Formula 14.

[Chemical Forula 14]

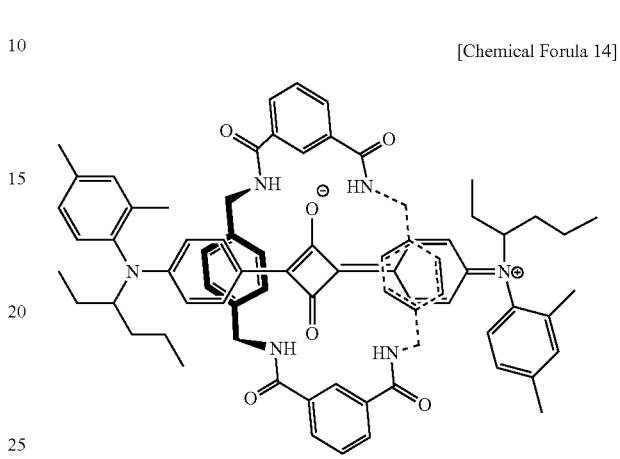

Maldi-tof MS: 1173.51 m/z

Synthesis Example 17: Synthesis of Core-Shell Dye Represented by Chemical Formula 15

The compound represented by Chemical Formula 1-5 (5 mmol) is dissolved in 600 mL of a chloroform solvent, and triethylamine (50 mmol) is added thereto. 2,6-pyridinedicarbonyl dichloride (20 mmol) and p-xylylene diamine (20 mmol) were dissolved in 60 mL of chloroform, and the obtained solution was added to the above solution in a dropwise fashion at room temperature for 5 hours. After 12 hours, the obtained mixture was distilled under a reduced pressure and separated through column chromatography to synthesize a core-shell dye represented by Chemical Formula 15.

[Chemical Formula 15]

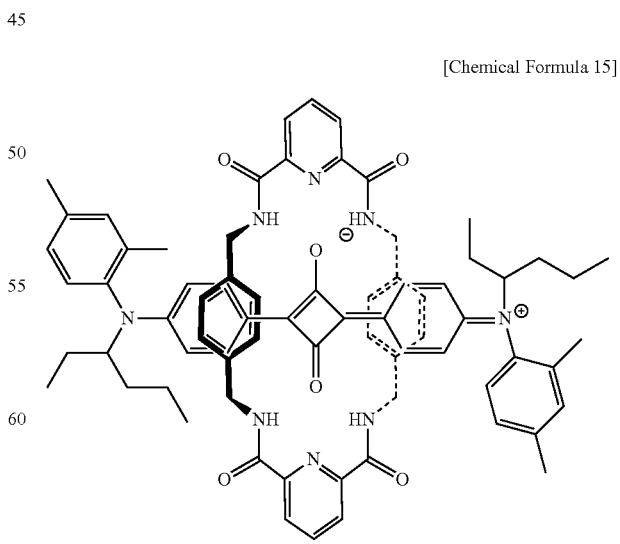

Maldi-tof MS: 1175.49 m/z

Synthesis Example 18: Synthesis of Core-Shell Dye Represented by Chemical Formula 16

The compound represented by Chemical Formula 1-6 (5 mmol) was dissolved in 600 mL of a chloroform solvent, and a solution obtained by dissolving isophthaloyl chloride (20 mmol) and p-xylylene diamine (20 mmol) in 60 mL of chloroform was added thereto in a dropwise fashion at room temperature for 5 hours. After 12 hours, the obtained mixture was distilled under a reduced pressure and separated through column chromatography to synthesize a core-shell dye represented by Chemical Formula 16.

[Chemical Formula 16]

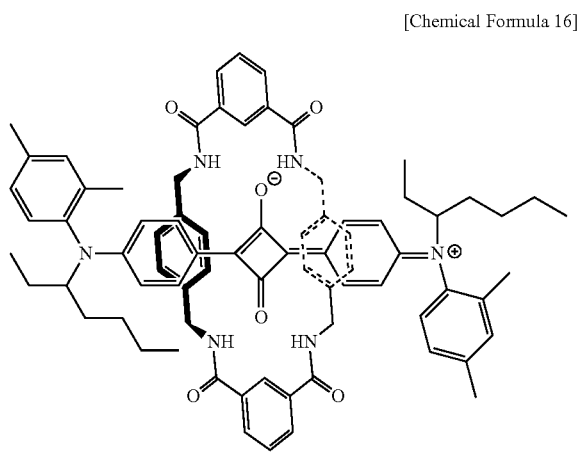

Maldi-tof MS: 1201.57 m/z

Synthesis Example 19: Synthesis of Core-Shell Dye Represented by Chemical Formula 17

The compound represented by Chemical Formula 1-6 (5 mmol) was dissolved in 600 mL of a chloroform solvent, and triethylamine (50 mmol) was added thereto. 2,6-pyridinedicarbonyl dichloride (20 mmol) and p-xylylene diamine (20 mmol) were dissolved in 60 mL of chloroform, and the obtained solution was added in a dropwise fashion to the above solution at room temperature for 5 hours. After 12 hours, the obtained mixture was distilled under a reduced pressure and separated through column chromatography to synthesize a core-shell dye represented by Chemical Formula 17.

[Chemical Formula 17]

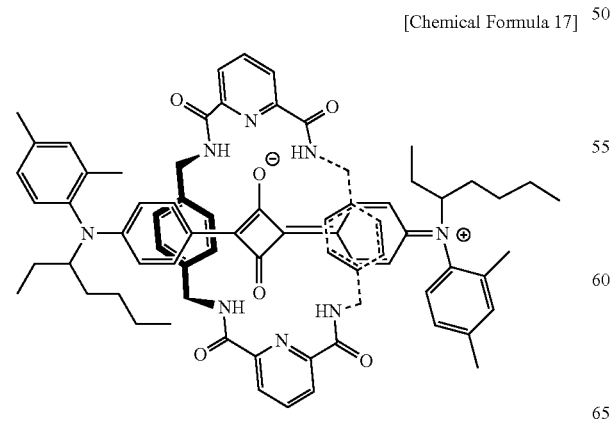

Maldi-tof MS: 1203.54 m/z

Synthesis Example 20: Synthesis of Core-Shell Dye Represented by Chemical Formula 18

The compound represented by Chemical Formula 1-7 (5 mmol) was dissolved in 600 mL of a chloroform solvent, and a solution obtained by dissolving isophthaloyl chloride (20 mmol) and p-xylylene diamine (20 mmol) in 60 mL of chloroform was added in a dropwise fashion thereto at room temperature for 5 hours. After 12 hours, the obtained mixture was distilled under a reduced pressure and separated through column chromatography to synthesize a core-shell dye represented by Chemical Formula 18.

[Chemical Formula 18]

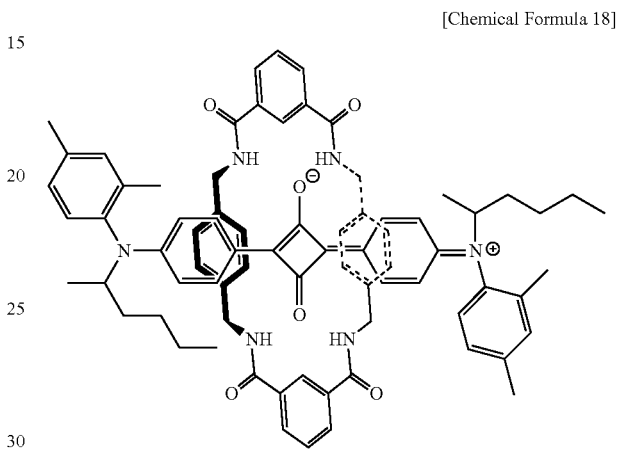

Maldi-tof MS: 1173.51 m/z

Synthesis Example 21: Synthesis of Core-Shell Dye Represented by Chemical Formula 19

The compound represented by Chemical Formula 1-7 (5 mmol) was dissolved in 600 mL of a chloroform solvent, and triethylamine (50 mmol) was added thereto. 2,6-pyridinedicarbonyl dichloride (20 mmol) and p-xylylene diamine (20 mmol) were dissolved in 60 mL of chloroform, and the obtained solution was added to the above solution in a dropwise fashion at room temperature for 5 hours. After 12 hours, the obtained mixture was distilled under a reduced pressure and separated through column chromatography to synthesize a core-shell dye represented by Chemical Formula 19.

[Chemical Formula 19]

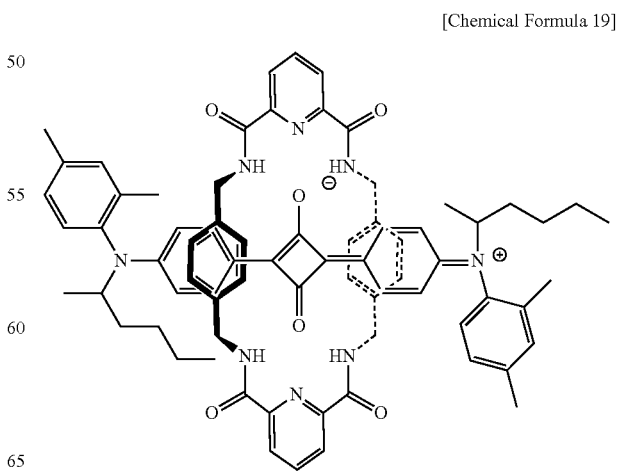

Maldi-tof MS: 1176.50 m/z

Comparative Synthesis Example 1: Synthesis of Core-Shell Dye 398 mg of squaric acid and 2.23 g of 2-(3-(dibutylamino)phenoxy)ethyl acrylate were put in a 100 mL 3-necked flask, 40 mL of n-butanol and 20 mL of toluene were added thereto, and the mixture was heated and refluxed at 120° C. for 5 hours. Water produced during a reaction was removed by using a Dean-Stark trap set, and the reaction was promoted. When the reaction was complete, a resultant therefrom was cooled down and then, extracted with methylene chloride and treated through column chromatography to synthesize a compound represented by Chemical Formula X at a yield of 60%. Subsequently, 0.72 g (1 mmol) of the compound represented by Chemical Formula X and 2.02 g (1 mmol) of triacetyl β-cyclodextrin represented by Chemical Formula Y (CAS #23739-88-0, TCI) were dissolved in 50 ml of dichloromethane, and the solution was stirred for about 12 hours at room temperature and then, after completely removing the solvent under a reduced pressure, dried to obtain about 2.7 g of a core-shell dye in a solid state. The core-shell dye had a structure that the compound represented by Chemical Formula Y surrounded the compound represented by Chemical Formula X.

[Chemical Formula X]

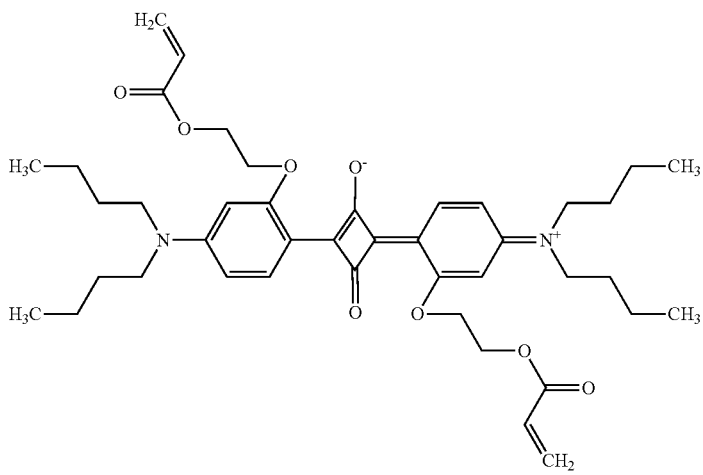

[Chemical Formula Y]

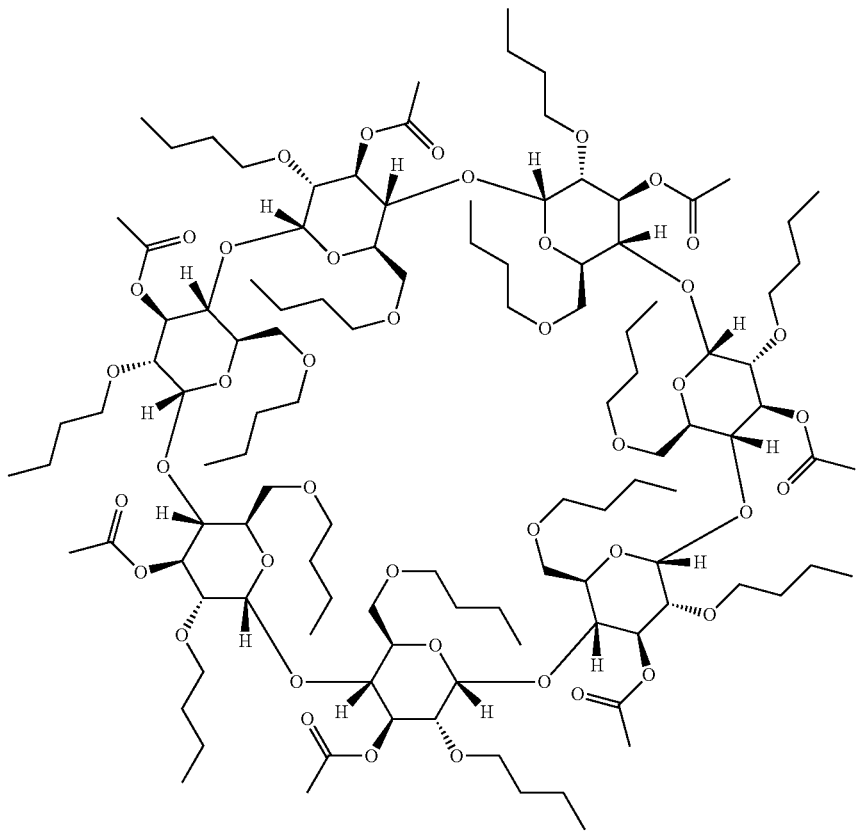

Comparative Synthesis Example 2: Synthesis of Compound Represented by Chemical Formula Z

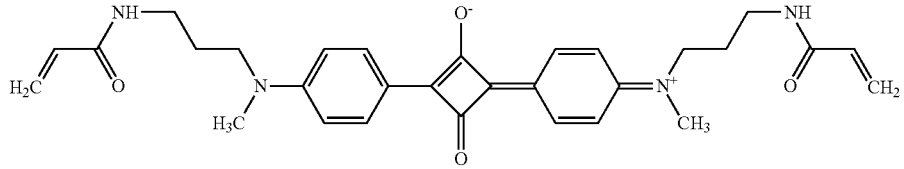

[Chemical Formula Z]

398 mg of squaric acid and 2.23 g of 2-(3-(methyl(phenyl)amino)propylamino)ethyl acrylate were put in a 100 mL 3-necked flask, 40 mL of n-butanol and 20 mL of toluene were added thereto, and the obtained mixture was heated and refluxed at 120° C. for 5 hours. Water produced during a reaction was removed by using a Dean-Stark trap set, and the reaction was promoted. When the reaction was complete, a resultant therefrom was cooled down and then, extracted with methylene chloride and treated through column chromatography to obtain a compound represented by Chemical Formula Z at a yield of 60%.

Maldi-tof MS: 514.26 m/z

Comparative Synthesis Example 3: Synthesis of Compound Represented by Chemical Formula 101

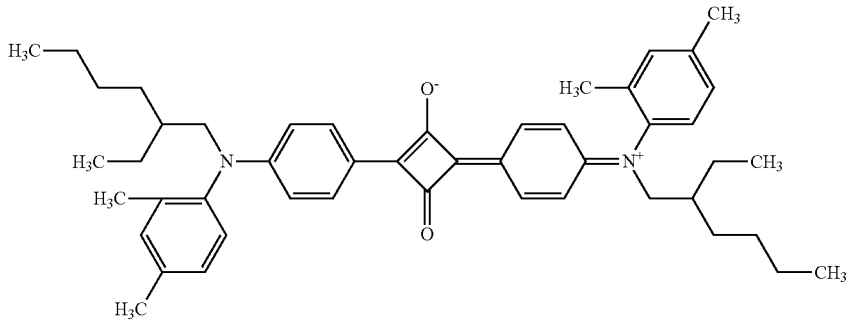

[Chemical Formula 101]

(2,4-Dimethyl-phenyl)-(2-ethyl-hexyl)-phenyl-amine (60 mmol) and 3,4-dihydroxy-3-cyclobutene-1,2-dione (30 mmol) were added to toluene (200 mL) and butanol (200 mL), and water generated by refluxing the mixture was removed with a Dean-stark distillator. After 12 hours, a green product therefrom was distilled under a reduced pressure and purified through column chromatography to synthesize a compound represented by Chemical Formula 101.

Maldi-tof MS: 697.02 m/z

Comparative Synthesis Example 4: Synthesis of Compound Represented by Chemical Formula 102

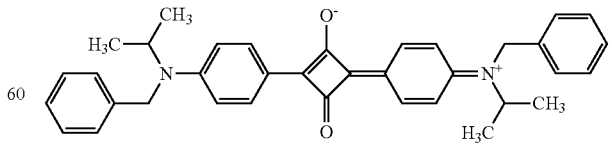

[Chemical Formula 102]

Benzyl-isopropyl-phenyl-amine (60 mmol) and 3,4-dihydroxy-3-cyclobutene-1,2-dione (30 mmol) were added to toluene (200 mL) and butanol (200 mL), and water generated by refluxing the mixture was removed with a Dean-stark distillator. After stirred for 12 hours, a green reactant therefrom was distilled under a reduced pressure and purified through column chromatography to synthesize a compound represented by Chemical Formula 102.

Maldi-tof MS: 528.70 m/z

Comparative Synthesis Example 5: Synthesis of Compound Represented by Chemical Formula 103

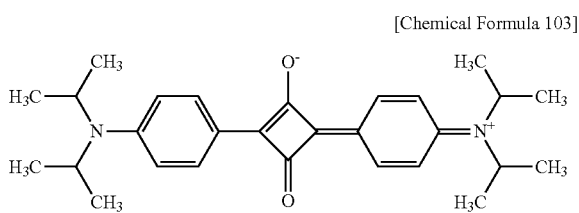 [SMILES: CC(C)N(c1ccc(C2=C([O-])C(=C3C=CC(=[N+](C(C)C)C(C)C)C=C3)C2=O)cc1)C(C)C]

[Chemical Formula 103]

Diisopropyl-phenyl-amine (60 mmol) and 3,4-dihydroxy-3-cyclobutene-1,2-dione (30 mmol) were added to toluene (200 mL) and butanol (200 mL), and water generated by refluxing the mixture was removed with a Dean-stark distillator. After stirred for 12 hours, a green product therefrom was distilled under a reduced pressure and purified through column chromatography to synthesize a compound represented by Chemical Formula 103.

Maldi-tof MS: 432.61 m/z

Comparative Synthesis Example 6: Synthesis of Compound Represented by Chemical Formula 104

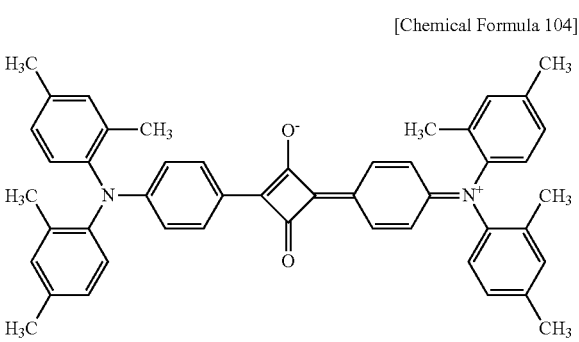 [SMILES: Cc1ccc(N(c2ccc(C3=C([O-])C(=C4C=CC(=[N+](c5ccc(C)cc5C)c5ccc(C)cc5C)C=C4)C3=O)cc2)c2ccc(C)cc2C)c(C)c1]

[Chemical Formula 104]

Bis-(2,4-dimethyl-phenyl)-phenyl-amine (60 mmol) and 3,4-dihydroxy-3-cyclobutene-1,2-dione (30 mmol) were added to toluene (200 mL) and butanol (200 mL), and water produced by refluxing the mixture was removed with a Dean-stark distillator. After stirred for 12 hours, a green product therefrom was distilled under a reduced pressure and purified through column chromatography to synthesize a compound represented by Chemical Formula 104.

Maldi-tof MS: 680.89 m/z

Preparation of Photosensitive Resin Composition

Photosensitive resin compositions were prepared using the following components.

(A) Dye (A-1) Compound prepared in Synthesis Example 1 (represented by Chemical Formula 1-1)

(A-2) Compound prepared in Synthesis Example 2 (represented by Chemical Formula 1-2)

(A-3) Compound prepared in Synthesis Example 3 (represented by Chemical Formula 1-3)

(A-4) Compound prepared in Synthesis Example 4 (represented by Chemical Formula 1-4)

(A-5) Compound prepared in Synthesis Example 5 (represented by Chemical Formula 1-5)

(A-6) Compound prepared in Synthesis Example 6 (represented by Chemical Formula 1-6)

(A-7) Compound prepared in Synthesis Example 7 (represented by Chemical Formula 1-7)

(A-8) Core-shell dye prepared in Synthesis Example 8 (represented by Chemical Formula 6)

(A-9) Core-shell dye prepared in Synthesis Example 9 (represented by Chemical Formula 7)

(A-10) Core-shell dye prepared in Synthesis Example 10 (represented by Chemical Formula 8)

(A-11) Core-shell dye prepared in Synthesis Example 11 (represented by Chemical Formula 9)

(A-12) Core-shell dye prepared in Synthesis Example 12 (represented by Chemical Formula 10)

(A-13) Core-shell dye prepared in Synthesis Example 13 (represented by Chemical Formula 11)

(A-14) Core-shell dye prepared in Synthesis Example 14 (represented by Chemical Formula 12)

(A-15) Core-shell dye prepared in Synthesis Example 15 (represented by Chemical Formula 13)

(A-16) Core-shell dye prepared in Synthesis Example 16 (represented by Chemical Formula 14)

(A-17) Core-shell dye prepared in Synthesis Example 17 (represented by Chemical Formula 15)

(A-18) Core-shell dye prepared in Synthesis Example 18 (represented by Chemical Formula 16)

(A-19) Core-shell dye prepared in Synthesis Example 19 (represented by Chemical Formula 17)

(A-20) Core-shell dye prepared in Synthesis Example 20 (represented by Chemical Formula 18)

(A-21) Core-shell dye prepared in Synthesis Example 21 (represented by Chemical Formula 19)

(A-22) Core-shell dye prepared in Comparative Synthesis Example 1

(A-23) Compound prepared in Comparative Synthesis Example 2 (represented by Chemical Formula Z)

(A-24) Compound prepared in Comparative Synthesis Example 3 (represented by Chemical Formula 101)

(A-25) Compound prepared in Comparative Synthesis Example 4 (represented by Chemical Formula 102)

(A-26) Compound prepared in Comparative Synthesis Example 5 (represented by Chemical Formula 103)

(A-27) Compound prepared in Comparative Synthesis Example 6 (represented by Chemical Formula 104)

(A') Pigment Dispersion Liquid (A'-1) C.I. green pigment 7

(A'-2) C.I. green pigment 36

(B) Binder Resin

A methacrylic acid/benzylmethacrylate copolymer having a weight average molecular weight of 22,000 g/mol (a mixing weight ratio: 15 wt %/85 wt %)

(C) Photopolymerizable Monomer

Dipentaerythritolhexaacrylate (D) Photopolymerization Initiator (D-1) 1,2-octandione (D-2) 2-dimethylamino-2-(4-methyl-benzyl)-1-(4-morpholin-4-yl-phenyl)-butan-1-one (E) Solvent (E-1) Cyclohexanone (E-2) Propylene glycol monomethylether acetate Examples 1 to 21 and Comparative Examples 1 to 8

Photosensitive resin compositions were prepared by mixing each component in the compositions shown in Table 1 to Table 4. Specifically, a photopolymerization initiator was dissolved in a solvent, the solution was stirred at room temperature for 2 hours, a dye (or pigment dispersion liquid) was added thereto, the mixture was stirred for 30 minutes, a binder resin and a photopolymerizable monomer were added thereto, and the obtained mixture was stirred at room temperature for 2 hours. The solution was three times filtered to remove impurities and prepare a photosensitive resin composition.

TABLE 1

(unit: wt %)

|  |  | Examples |  |  |  |  |  |  |  |  |
|---|---|---|---|---|---|---|---|---|---|---|
|  |  | 1 | 2 | 3 | 4 | 5 | 6 | 7 | 8 | 9 |
| (A) Dye | A-1 | 2 | — | — | — | — | — | — | — | — |
|  | A-2 | — | 2 | — | — | — | — | — | — | — |
|  | A-3 | — | — | 2 | — | — | — | — | — | — |
|  | A-4 | — | — | — | 2 | — | — | — | — | — |
|  | A-5 | — | — | — | — | 2 | — | — | — | — |
|  | A-6 | — | — | — | — | — | 2 | — | — | — |
|  | A-7 | — | — | — | — | — | — | 2 | — | — |
|  | A-8 | — | — | — | — | — | — | — | 2 | — |
|  | A-9 | — | — | — | — | — | — | — | — | 2 |
| (A') Pigment dispersion liquid | A'-1 | — | — | — | — | — | — | — | — | — |
|  | A'-2 | — | — | — | — | — | — | — | — | — |
| (B) Binder resin |  | 3.5 | 3.5 | 3.5 | 3.5 | 3.5 | 3.5 | 3.5 | 3.5 | 3.5 |
| (C) Photopolymerizable monomer |  | 8 | 8 | 8 | 8 | 8 | 8 | 8 | 8 | 8 |
| (D) Photopolymerization initiator | D-1 | 1 | 1 | 1 | 1 | 1 | 1 | 1 | 1 | 1 |
|  | D-2 | 0.5 | 0.5 | 0.5 | 0.5 | 0.5 | 0.5 | 0.5 | 0.5 | 0.5 |
| (E) Solvent | E-1 | 40 | 40 | 40 | 40 | 40 | 40 | 40 | 40 | 40 |
|  | E-2 | 45 | 45 | 45 | 45 | 45 | 45 | 45 | 45 | 45 |
| Total |  | 100 | 100 | 100 | 100 | 100 | 100 | 100 | 100 | 100 |

TABLE 2

(unit: wt %)

|  |  | Examples |  |  |  |  |  |  |  |  |
|---|---|---|---|---|---|---|---|---|---|---|
|  |  | 10 | 11 | 12 | 13 | 14 | 15 | 16 | 17 | 18 |
| (A) Dye | A-10 | 2 | — | — | — | — | — | — | — | — |
|  | A-11 | — | 2 | — | — | — | — | — | — | — |
|  | A-12 | — | — | 2 | — | — | — | — | — | — |
|  | A-13 | — | — | — | 2 | — | — | — | — | — |
|  | A-14 | — | — | — | — | 2 | — | — | — | — |
|  | A-15 | — | — | — | — | — | 2 | — | — | — |
|  | A-16 | — | — | — | — | — | — | 2 | — | — |
|  | A-17 | — | — | — | — | — | — | — | 2 | — |
|  | A-18 | — | — | — | — | — | — | — | — | 2 |
| (A') Pigment dispersion liquid | A'-1 | — | — | — | — | — | — | — | — | — |
|  | A'-2 | — | — | — | — | — | — | — | — | — |
| (B) Binder resin |  | 3.5 | 3.5 | 3.5 | 3.5 | 3.5 | 3.5 | 3.5 | 3.5 | 3.5 |
| (C) Photopolymerizable monomer |  | 8 | 8 | 8 | 8 | 8 | 8 | 8 | 8 | 8 |
| (D) Photopolymerization initiator | D-1 | 1 | 1 | 1 | 1 | 1 | 1 | 1 | 1 | 1 |
|  | D-2 | 0.5 | 0.5 | 0.5 | 0.5 | 0.5 | 0.5 | 0.5 | 0.5 | 0.5 |
| (E) Solvent | E-1 | 40 | 40 | 40 | 40 | 40 | 40 | 40 | 40 | 40 |
|  | E-2 | 45 | 45 | 45 | 45 | 45 | 45 | 45 | 45 | 45 |
| Total |  | 100 | 100 | 100 | 100 | 100 | 100 | 100 | 100 | 100 |

TABLE 3

(unit: wt %)

|  |  | Examples | | | Comparative Examples | | | | | |
|---|---|---|---|---|---|---|---|---|---|---|
|  |  | 19 | 20 | 21 | 1 | 2 | 3 | 4 | 5 | 6 |
| (A) Dye | A-19 | 2 | — | — | — | — | — | — | — | — |
|  | A-20 | — | 2 | — | — | — | — | — | — | — |
|  | A-21 | — | — | 2 | — | — | — | — | — | — |
|  | A-22 | — | — | — | 2 | — | — | — | — | — |
|  | A-23 | — | — | — | — | 2 | — | — | — | — |
|  | A-24 | — | — | — | — | — | 2 | — | — | — |
|  | A-25 | — | — | — | — | — | — | 2 | — | — |
|  | A-26 | — | — | — | — | — | — | — | 2 | — |
|  | A-27 | — | — | — | — | — | — | — | — | 2 |
| (A') Pigment dispersion liquid | A'-1 | — | — | — | — | — | — | — | — | — |
|  | A'-2 | — | — | — | — | — | — | — | — | — |
| (B) Binder resin |  | 3.5 | 3.5 | 3.5 | 3.5 | 3.5 | 3.5 | 3.5 | 3.5 | 3.5 |
| (C) Photopolymerizable monomer |  | 8 | 8 | 8 | 8 | 8 | 8 | 8 | 8 | 8 |
| (D) Photopolymerization initiator | D-1 | 1 | 1 | 1 | 1 | 1 | 1 | 1 | 1 | 1 |
|  | D-2 | 0.5 | 0.5 | 0.5 | 0.5 | 0.5 | 0.5 | 0.5 | 0.5 | 0.5 |
| (E) Solvent | E-1 | 40 | 40 | 40 | 40 | 40 | 40 | 40 | 40 | 40 |
|  | E-2 | 45 | 45 | 45 | 45 | 45 | 45 | 45 | 45 | 45 |
| Total |  | 100 | 100 | 100 | 100 | 100 | 100 | 100 | 100 | 100 |

TABLE 4

(unit: wt %)

|  |  | Comparative Examples | |
|---|---|---|---|
|  |  | 7 | 8 |
| (A') Pigment dispersion liquid | A'-1 | 35 | — |
|  | A'-2 | — | 35 |
| (B) Binder resin |  | 2.5 | 2.5 |
| (C) Photopolymerizable monomer |  | 5 | 5 |
| (D) Photopolymerization initiator | D-1 | 1 | 1 |
|  | D-2 | 0.5 | 0.5 |
| (E) Solvent | E-1 | 40 | 40 |
|  | E-2 | 16 | 16 |
| Total |  | 100 | 100 |

(Evaluation)

Evaluation 1: Luminance and Contrast Ratio

The photosensitive resin compositions according to Example 1 to Example 21 and Comparative Example 1 to Comparative Example 8 were respectively coated to be 1 μm to 3 μm thick on a 1 mm-thick degreased glass substrate and dried on a 90° C. hot plate for 2 minutes to obtain films. Subsequently, the films were exposed to light with a high pressure mercury lamp having a main wavelength of 365 nm and dried in forced convection drying furnace of a 200° C. oven for 5 minutes. Luminance and contrast ratios of pixel layers were measured using a spectrophotometer (MCPD3000, Otsuka electronic Co., Ltd.) and the results are shown in Table 5.

TABLE 5

|  | Luminance | Contrast ratio |
|---|---|---|
| Example 1 | 65.1 | 14100 |
| Example 2 | 65.2 | 14500 |
| Example 3 | 65.4 | 14300 |
| Example 4 | 65.4 | 14500 |
| Example 5 | 65.5 | 14300 |
| Example 6 | 65.2 | 14500 |

TABLE 5-continued

|  | Luminance | Contrast ratio |
|---|---|---|
| Example 7 | 65.1 | 14200 |
| Example 8 | 67.2 | 14300 |
| Example 9 | 68.0 | 14900 |
| Example 10 | 67.3 | 14600 |
| Example 11 | 67.8 | 14200 |
| Example 12 | 67.3 | 14600 |
| Example 13 | 67.6 | 14200 |
| Example 14 | 67.4 | 14200 |
| Example 15 | 67.8 | 14700 |
| Example 16 | 67.4 | 14900 |
| Example 17 | 67.8 | 15000 |
| Example 18 | 67.3 | 14600 |
| Example 19 | 67.8 | 14200 |
| Example 20 | 67.1 | 14300 |
| Example 21 | 67.8 | 14900 |
| Comparative Example 1 | 64.1 | 13300 |
| Comparative Example 2 | 64.0 | 13800 |
| Comparative Example 3 | 64.6 | 13300 |
| Comparative Example 4 | 64.2 | 13200 |
| Comparative Example 5 | 64.6 | 13700 |
| Comparative Example 6 | 64.3 | 13700 |
| Comparative Example 7 | 62.6 | 12300 |
| Comparative Example 8 | 63.1 | 12000 |

Referring to Table 5, Example 1 to Example 21 including a monomolecular dye or a core-shell dye according to one embodiment of the present invention showed high luminance and a high contrast ratio compared with Comparative Example 1 to Comparative Example 8 including neither the monomolecular dye nor the core-shell dye.

Evaluation 2: Durability

The photosensitive resin compositions according to Example 8 to Example 21 and Comparative Example 1 to Comparative Example 8 were respectively coated to be 1 μm to 3 μm thick on a 1 mm-thick degreased glass substrate and dried on a 90° C. hot plate for 2 minutes to obtain films. The films were exposed to light with a high pressure mercury lamp having a main wavelength of 365 nm and dried in a 200° C. oven for 20 minutes, and a spectrophotometer (MCPD3000, Otsuka Electronics Co., Ltd.) to measure color coordinate changes and thus evaluate durability, and the results are shown in Table 6.

Evaluation Reference of Durability

○: color coordinate change of less than 0.003

Δ: color coordinate change of greater than or equal to 0.003 and less than or equal to 0.005

X: color coordinate change of greater than 0.005

TABLE 6

|  | Durability |
|---|---|
| Example 8 | ○ |
| Example 9 | ○ |
| Example 10 | ○ |
| Example 11 | ○ |
| Example 12 | ○ |
| Example 13 | ○ |
| Example 14 | ○ |
| Example 15 | ○ |
| Example 16 | ○ |
| Example 17 | ○ |
| Example 18 | ○ |
| Example 19 | ○ |
| Example 20 | ○ |
| Example 21 | ○ |
| Comparative Example 1 | X |
| Comparative Example 2 | X |
| Comparative Example 3 | Δ |
| Comparative Example 4 | Δ |
| Comparative Example 5 | Δ |
| Comparative Example 6 | X |
| Comparative Example 7 | X |
| Comparative Example 8 | X |

Referring to Table 6, Example 8 to Example 21 including a core-shell dye according to an embodiment showed excellent durability compared with Comparative Example 1 to Comparative Example 8 without the core-shell dye.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

What is claimed is:

1. A compound represented by Chemical Formula 1:

[Chemical Formula 1]

wherein, in Chemical Formula 1, $R^1$ is a substituted or unsubstituted C3 to C20 cycloalkyl group or represented by Chemical Formula 2, and $R^2$ is a substituted C6 to C20 aryl group,

[Chemical Formula 2]

wherein, in Chemical Formula 2, $R^3$ and $R^4$ are independently a substituted or unsubstituted C1 to C10 alkyl group.

2. The compound of claim 1, wherein $R^2$ is a C6 to C20 aryl group substituted with a C1 to C10 alkyl group.

3. The compound of claim 2, wherein $R^2$ is represented by Chemical Formula 3:

[Chemical Formula 3]

wherein, in Chemical Formula 3, $R^5$ and $R^6$ are independently a C1 to C7 alkyl group.

4. The compound of claim 1, wherein the compound represented by Chemical Formula 1 is represented by one selected from compounds represented by Chemical Formula 1-1 to Chemical Formula 1-7

[Chemical Formula 1-1]

[Chemical Formula 1-2]

-continued

[Chemical Formula 1-3]

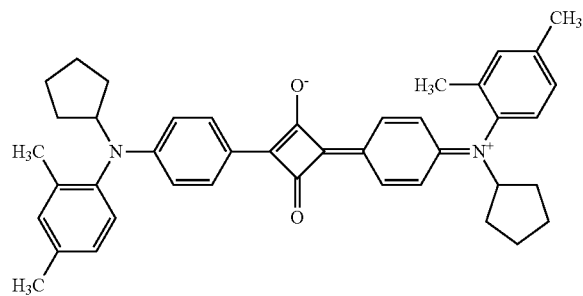

[Chemical Formula 1-4]

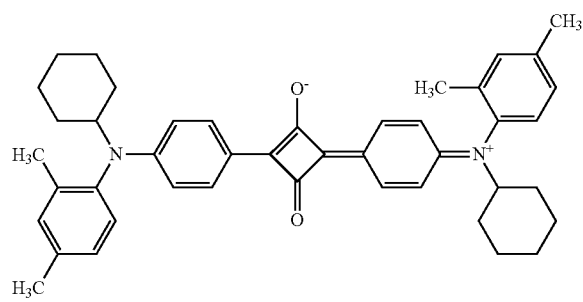

[Chemical Formula 1-5]

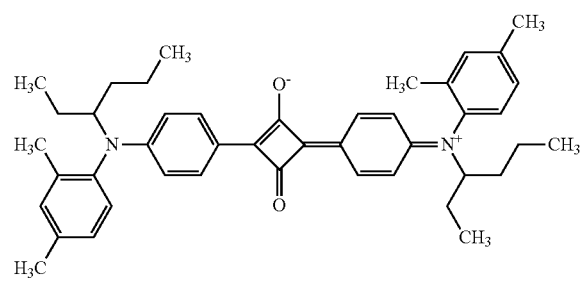

[Chemical Formula 1-6]

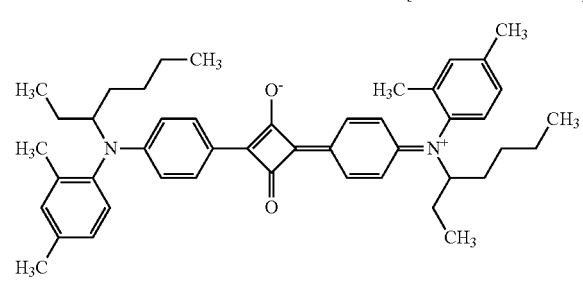

[Chemical Formula 1-7]

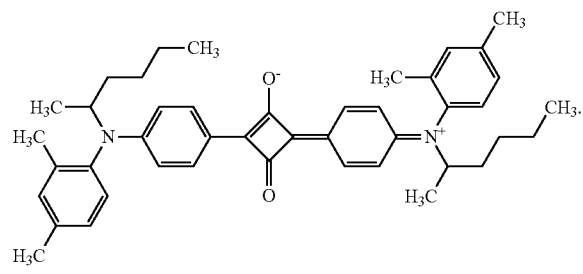

5. A core-shell dye comprising
a core including the compound of claim 1; and
a shell surrounding the core.

6. The core-shell dye of claim 5, wherein the shell is represented by Chemical Formula 4 or Chemical Formula 5:

[Chemical Formula 4]

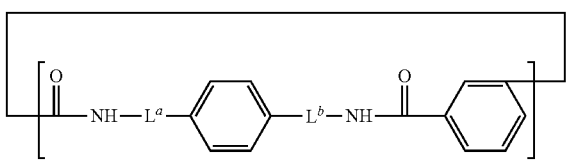

[Chemical Formula 5]

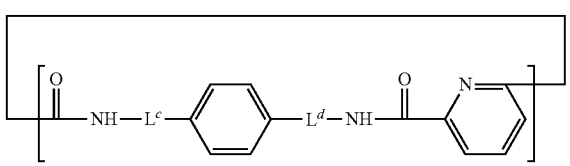

wherein, in Chemical Formula 4 and Chemical Formula 5,
$L^a$ to $L^d$ are independently a single bond or a substituted or unsubstituted C1 to C10 alkylene group.

7. The core-shell dye of claim 6, wherein the $L^a$ to $L^d$ are independently a substituted or unsubstituted C1 to C10 alkylene group.

8. The core-shell dye of claim 5, wherein the shell is represented by Chemical Formula 4-1 or Chemical Formula 5-1:

[Chemical Formula 4-1]

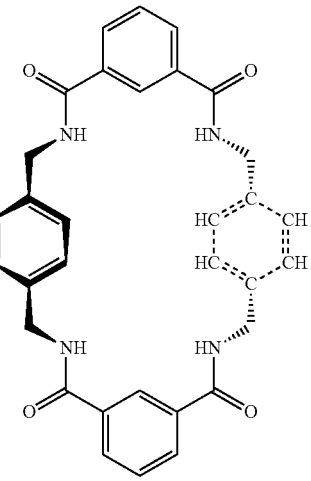

[Chemical Formula 5-1]

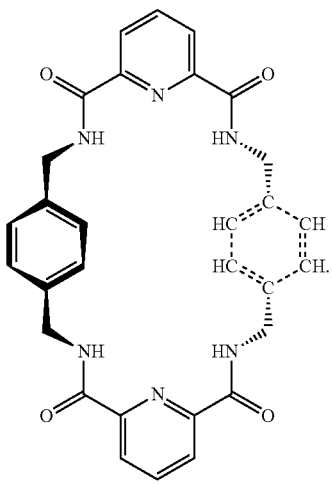

9. The core-shell dye of claim 8, wherein the shell has a cage width of 6.5 Å to 7.5 Å.

10. The core-shell dye of claim 5, wherein the core has a length of 1 nm to 3 nm.

11. The core-shell dye of claim 5, wherein the core has a maximum absorption peak in a wavelength of 530 nm to 680 nm.

12. The core-shell dye of claim 5, wherein the core-shell dye is selected from compounds represented by Chemical Formula 6 to Chemical Formula 19:

[Chemical Formula 6]

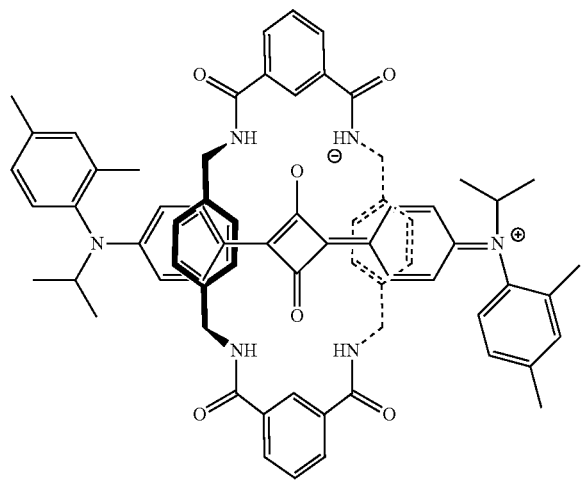

[Chemical Formula 7]

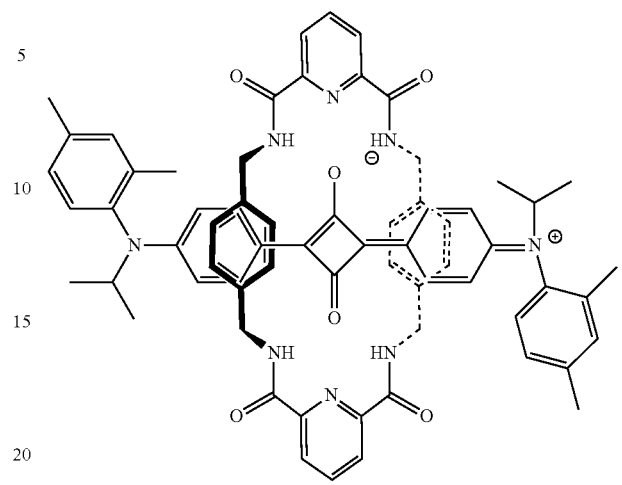

[Chemical Formula 8]

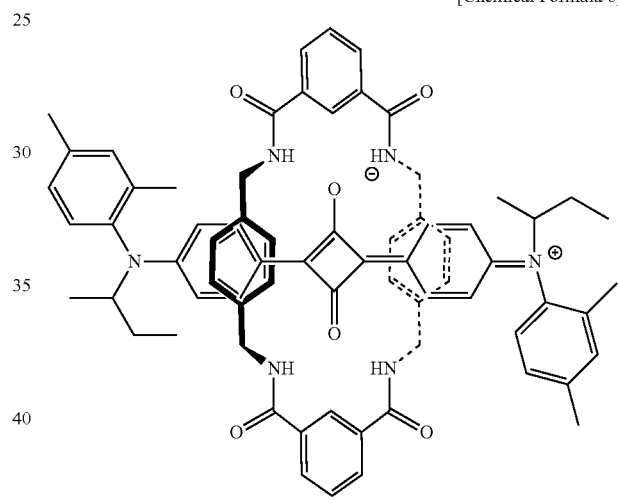

[Chemical Formula 9]

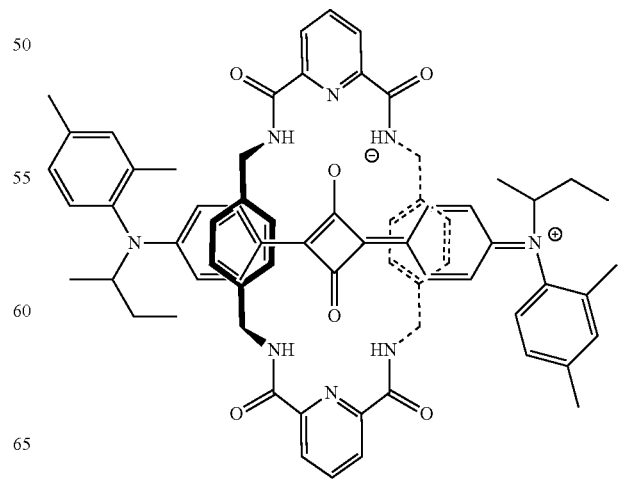

59
-continued
[Chemical Formula 10]
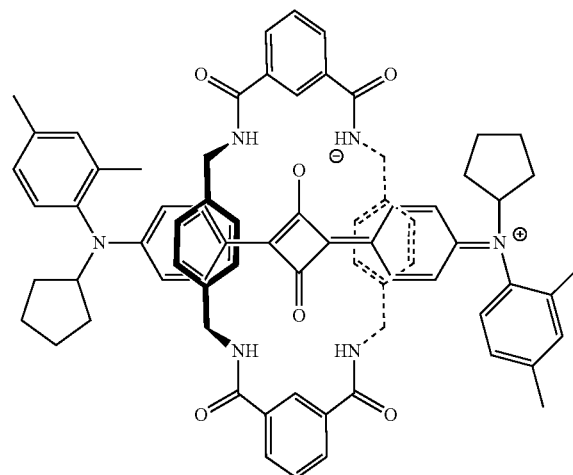
[Chemical Formula 11]
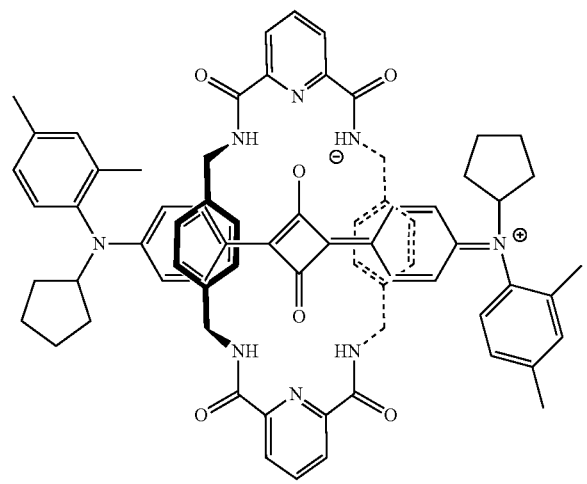
[Chemical Formula 12]
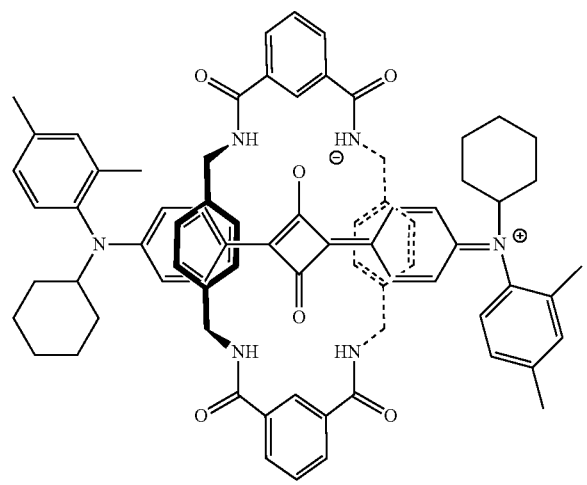
60
-continued
[Chemical Formula 13]
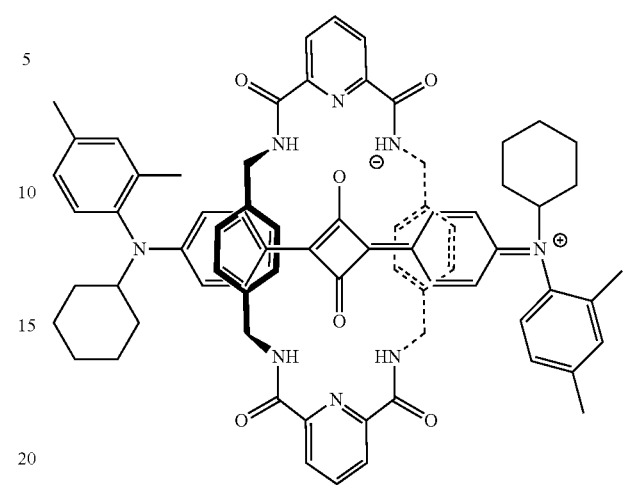
[Chemical Formula 14]
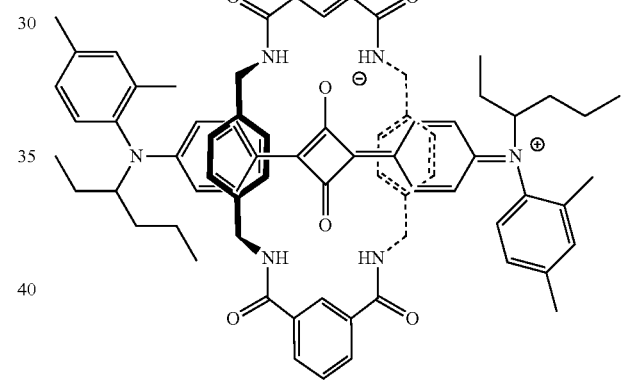
[Chemical Formula 15]
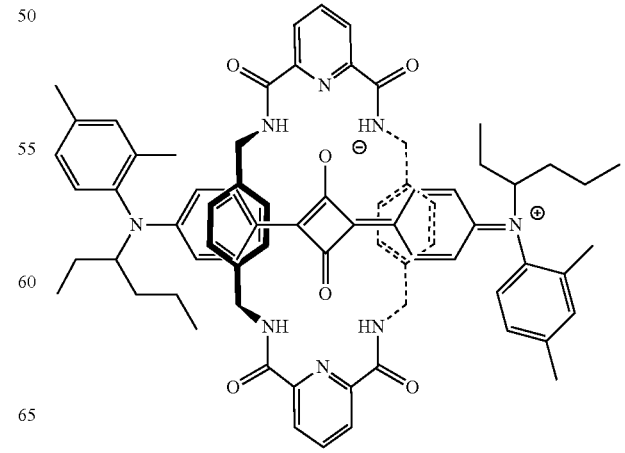

-continued

[Chemical Formula 16]

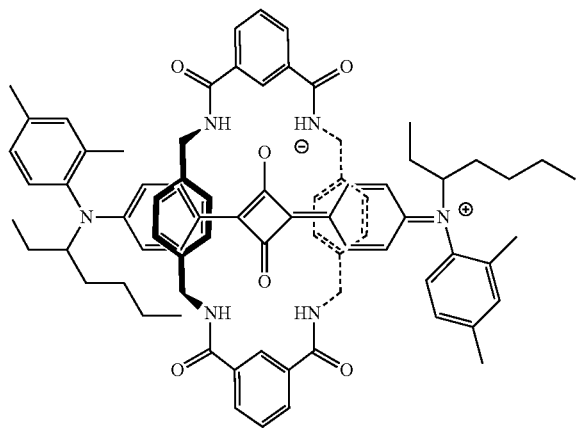

[Chemical Formula 17]

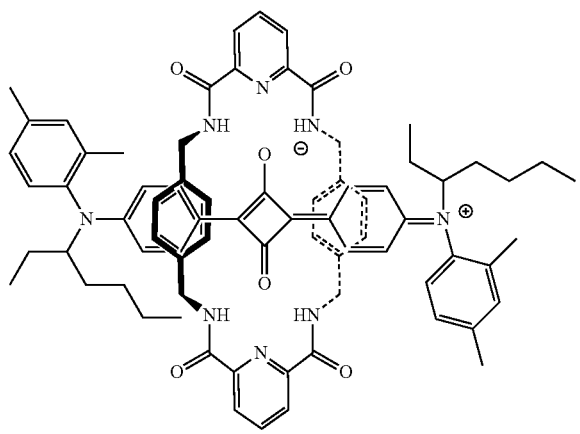

[Chemical Formula 18]

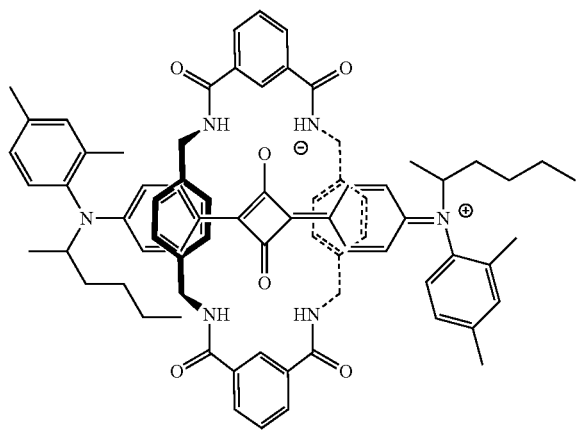

-continued

[Chemical Formula 19]

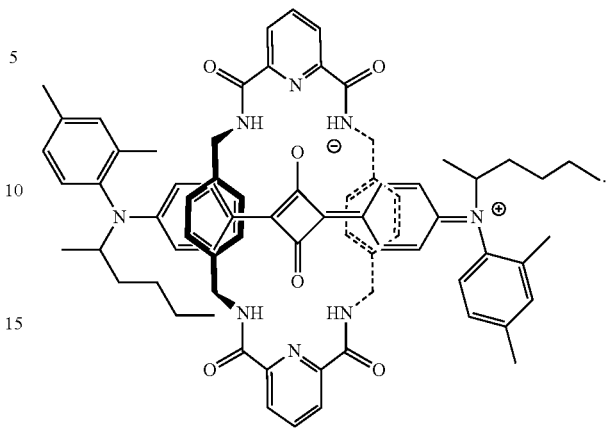

13. The core-shell dye of claim 5, wherein the core-shell dye includes the core and the shell in a mole ratio of 1:1.

14. The core-shell dye of claim 5, wherein the core-shell dye is a green dye.

15. A photosensitive resin composition comprising the compound of claim 1.

16. The photosensitive resin composition of claim 15, wherein the photosensitive resin composition further includes a binder resin, a photopolymerizable monomer, a photopolymerization initiator, and a solvent.

17. The photosensitive resin composition of claim 16, wherein the photosensitive resin composition further includes a pigment.

18. The photosensitive resin composition of claim 16, wherein the photosensitive resin composition includes 0.5 wt % to 10 wt % of the compound;

0.1 wt % to 30 wt % of the binder resin;

0.1 wt % to 30 wt % of the photopolymerizable monomer;

0.1 wt % to 5 wt % of the photopolymerization initiator; and a balance amount of the solvent based on a total amount of the photosensitive resin composition.

19. The photosensitive resin composition of claim 16, wherein the photosensitive resin composition further includes malonic acid, 3-amino-1,2-propanediol, a silane-based coupling agent including a vinyl group or a (meth)acryloxy group, a leveling agent, a surfactant, a radical polymerization initiator, or a combination thereof.

20. A color filter manufactured using the photosensitive resin composition of claim 15.

* * * * *